(12) United States Patent
Dalvi et al.

(10) Patent No.: US 12,150,760 B2
(45) Date of Patent: *Nov. 26, 2024

(54) NON-INVASIVE OPTICAL PHYSIOLOGICAL DIFFERENTIAL PATHLENGTH SENSOR

(71) Applicant: Willow Laboratories, Inc., Irvine, CA (US)

(72) Inventors: Cristiano Dalvi, Lake Forest, CA (US); Ferdyan Lesmana, Irvine, CA (US); Hung The Vo, Fountain Valley, CA (US); Jeroen Poeze, Rancho Santa Margarita, CA (US); Jesse Chen, Foothill Ranch, CA (US); Kevin Hughes Pauley, Lake Forest, CA (US); Mathew Paul, Irvine, CA (US); Sean Merritt, Lake Forest, CA (US); Thomas B. Blank, Laguna Beach, CA (US); Massi Joe E. Kiani, Laguna Niguel, CA (US)

(73) Assignee: Willow Laboratories, Inc., Irvine, CA (US)

( * ) Notice: Subject to any disclaimer, the term of this patent is extended or adjusted under 35 U.S.C. 154(b) by 43 days.

This patent is subject to a terminal disclaimer.

(21) Appl. No.: 18/066,118

(22) Filed: Dec. 14, 2022

(65) Prior Publication Data
US 2023/0181068 A1 Jun. 15, 2023

Related U.S. Application Data

(63) Continuation of application No. 15/160,907, filed on May 20, 2016, now Pat. No. 11,653,862.
(Continued)

(51) Int. Cl.
A61B 5/1455 (2006.01)
A61B 5/00 (2006.01)

(52) U.S. Cl.
CPC ........ *A61B 5/14552* (2013.01); *A61B 5/0075* (2013.01); *A61B 5/6838* (2013.01); *A61B 2562/0238* (2013.01)

(58) Field of Classification Search
None
See application file for complete search history.

(56) References Cited

U.S. PATENT DOCUMENTS 3,628,525 A * 12/1971 Polanyi .............. A61B 5/02416
356/41
4,960,128 A 10/1990 Gordon et al.
(Continued)

FOREIGN PATENT DOCUMENTS

WO WO 2016/191307 12/2016

OTHER PUBLICATIONS

US 2022/0192529 A1, 06/2022, Al-Ali et al. (withdrawn)
(Continued)

Primary Examiner — Jay B Shah
(74) Attorney, Agent, or Firm — Knobbe, Martens, Olson & Bear, LLP

(57) ABSTRACT

An optical physiological sensor configured to perform high speed spectral sweep analysis of sample tissue being measured to non-invasively predict an analyte level of a patient. An emitter of the optical physiological sensor can be regulated to operate at different temperatures to emit radiation at different wavelengths. Variation in emitter drive current, duty cycle, and forward voltage can also be used to cause the emitter to emit a range of wavelengths. Informative spectral data can be obtained during the sweeping of specific wavelength regions of sample tissue.

20 Claims, 12 Drawing Sheets

Related U.S. Application Data

(60) Provisional application No. 62/233,126, filed on Sep. 25, 2015, provisional application No. 62/165,618, filed on May 22, 2015.

(56) References Cited

U.S. PATENT DOCUMENTS

| | | |
|---|---|---|
| 4,964,408 A | 10/1990 | Hink et al. |
| 5,041,187 A | 8/1991 | Hink et al. |
| 5,069,213 A | 12/1991 | Hink et al. |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,424,545 A | 6/1995 | Block et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,353,226 B1 | 3/2002 | Khalil et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,403,944 B1 | 6/2002 | MacKenzie et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,678,543 B2 | 1/2004 | Diab et al. |
| 6,684,090 B2 | 1/2004 | Ali et al. |
| 6,684,091 B2 | 1/2004 | Parker |

(56) References Cited

U.S. PATENT DOCUMENTS

| | | |
|---|---|---|
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,882,874 B2 | 4/2005 | Huiku |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |

(56) References Cited

U.S. PATENT DOCUMENTS

| | | |
|---|---|---|
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |

(56) References Cited

U.S. PATENT DOCUMENTS

| | | |
|---|---|---|
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |

(56) References Cited

U.S. PATENT DOCUMENTS

| | | |
|---|---|---|
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |

(56) References Cited

U.S. PATENT DOCUMENTS

| | | |
|---|---|---|
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2004/0127779 A1 | 7/2004 | Steuer et al. |
| 2005/0055276 A1 | 3/2005 | Kiani et al. |
| 2005/0234317 A1 | 10/2005 | Kiani |
| 2005/0259254 A1 | 11/2005 | Soller et al. |
| 2006/0073719 A1 | 4/2006 | Kiani |
| 2006/0189871 A1 | 8/2006 | Al-Ali et al. |
| 2006/0211924 A1 | 9/2006 | Dalke et al. |
| 2006/0281982 A1 | 12/2006 | Grata et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2009/0036759 A1 | 2/2009 | Ault et al. |
| 2009/0054908 A1 | 2/2009 | Zand et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0016689 A1 | 1/2010 | Kanayama et al. |
| 2010/0030039 A1 | 2/2010 | Lamego et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0087083 A1 | 4/2011 | Poeze et al. |
| 2011/0105854 A1 | 5/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237969 A1 | 9/2011 | Eckerbom et al. |
| 2011/0288383 A1 | 11/2011 | Diab |
| 2011/0301444 A1 | 12/2011 | Al-Ali |
| 2012/0041316 A1 | 2/2012 | Al Ali et al. |
| 2012/0046557 A1 | 2/2012 | Kiani |
| 2012/0059267 A1 | 3/2012 | Lamego et al. |
| 2012/0078473 A1 | 3/2012 | Ridder et al. |
| 2012/0088984 A1 | 4/2012 | Al-Ali et al. |
| 2012/0123231 A1 | 5/2012 | O'Reilly |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0248985 A1 | 10/2012 | Lin et al. |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0190581 A1 | 7/2013 | Al-Ali et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0262730 A1 | 10/2013 | Al-Ali et al. |
| 2013/0267804 A1 | 10/2013 | Al-Ali |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0331660 A1 | 12/2013 | Al-Ali et al. |
| 2013/0331670 A1 | 12/2013 | Kiani |
| 2013/0345921 A1 | 12/2013 | Al-Ali et al. |
| 2014/0012100 A1 | 1/2014 | Al-Ali et al. |
| 2014/0034353 A1 | 2/2014 | Al-Ali et al. |
| 2014/0051953 A1 | 2/2014 | Lamego et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0155712 A1 | 6/2014 | Lamego et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194766 A1 | 7/2014 | Al-Ali et al. |
| 2014/0206963 A1 | 7/2014 | Al-Ali |
| 2014/0213864 A1 | 7/2014 | Abdul-Hafiz et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0303520 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |

(56) References Cited

U.S. PATENT DOCUMENTS

| | | |
|---|---|---|
| 2014/0330099 A1 | 11/2014 | Al-Ali et al. |
| 2014/0336481 A1 | 11/2014 | Shakespeare et al. |
| 2014/0336483 A1 | 11/2014 | Abee |
| 2014/0357966 A1 | 12/2014 | Al-Ali et al. |
| 2014/0371548 A1 | 12/2014 | Al-Ali et al. |
| 2014/0371632 A1 | 12/2014 | Al-Ali et al. |
| 2014/0378784 A1 | 12/2014 | Kiani et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Muhsin et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0140863 A1 | 5/2015 | Al-Ali et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank et al. |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali |
| 2016/0139040 A1 | 5/2016 | Case |
| 2016/0143548 A1 | 5/2016 | Al-Ali |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0283665 A1 | 9/2016 | Sampath et al. |
| 2016/0367173 A1 | 12/2016 | Dalvi et al. |
| 2017/0024748 A1 | 1/2017 | Haider |
| 2017/0042488 A1 | 2/2017 | Muhsin |
| 2017/0055896 A1 | 3/2017 | Al-Ali |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0103874 A1 | 4/2018 | Lee et al. |
| 2018/0199871 A1 | 7/2018 | Pauley et al. |
| 2018/0213583 A1 | 7/2018 | Al-Ali |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0058843 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |

(56) References Cited

U.S. PATENT DOCUMENTS

| | | |
|---|---|---|
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |

OTHER PUBLICATIONS

US 2024/0016391 A1, 01/2024, Lapotko et al. (withdrawn)
International Search Report and Written Opinion in PCT Application No. PCT/US2016/033622, dated Nov. 7, 2016.
USB2000 Fiber Optic Spectrometer: Installation and Operation Manual, Document No. 170-00000-000-02-1005, Ocean Optics, Inc., 2005, pp. 43.

\* cited by examiner

NON-INVASIVE OPTICAL PHYSIOLOGICAL DIFFERENTIAL PATHLENGTH SENSOR

INCORPORATION BY REFERENCE TO ANY PRIORITY APPLICATIONS

This application is a continuation of U.S. Non-Provisional application Ser. No. 15/160,907, filed May 20, 2016, titled "NON-INVASIVE OPTICAL PHYSIOLOGICAL DIFFERENTIAL PATHLENGTH SENSOR", which claims priority benefit under 35 U.S.C. § 119(e) of U.S. Provisional Application No. 62/165,618, filed May 22, 2015, titled "NON-INVASIVE OPTICAL PHYSIOLOGICAL SENSOR," and U.S. Provisional Application No. 62/233,126, filed Sep. 25, 2015, titled "NON-INVASIVE OPTICAL PHYSIOLOGICAL DIFFERENTIAL PATHLENGTH SENSOR," each of which is hereby incorporated by reference in its entirety. Any and all applications for which a foreign or domestic priority claim is identified in the Application Data Sheet as filed with the present application are hereby incorporated by reference under 37 CFR 1.57.

FIELD OF THE DISCLOSURE

The present disclosure relates to the field of non-invasive optical based physiological monitoring sensors that have a differential pathlength for the light to traverse through tissue.

BACKGROUND

Devices capable of spectroscopic analysis generally include a light source(s) characterized by a plurality of wavelengths of known spectra transmitting optical radiation into or reflecting off a measurement site, such as, body tissue carrying pulsing blood and/or interstitial fluid. After attenuation by tissue and fluids of the measurement site, a photo-detection device(s) detects the attenuated light and outputs a detector signal(s) responsive to the detected attenuated light. A signal processing device(s) process the detector(s) signal(s) and outputs a measurement indicative of a blood and/or interstitial fluid constituent of interest, such as glucose, oxygen, met-hemoglobin, total hemoglobin, other physiological parameters, or other data or combinations of data useful in determining a physiological state or trend of wellness of a patient.

SUMMARY

This disclosure describes embodiments of non-invasive methods, devices, and systems for measuring a blood and/or interstitial fluid constituent (which may also be referred to as an analyte), and/or substance such as oxygen, carboxyhemoglobin, methemoglobin, total hemoglobin, glucose, proteins, lipids, a percentage thereof (e.g., saturation), or for measuring many other physiologically relevant patient characteristics. These characteristics can relate, for example, to pulse rate, hydration, trending information and analysis, and the like.

In an embodiment, the system includes a non-invasive sensor and a patient monitor communicating with the non-invasive sensor. The non-invasive sensor may include different architectures to implement some or all of the disclosed features. In addition, an artisan will recognize that the non-invasive sensor may include or may be coupled to other components, such as a network interface, and the like. Moreover, the patient monitor may include a display device, a network interface communicating with anyone or combination of a computer network, a handheld computing device, a mobile phone, the Internet, or the like. In addition, embodiments may include multiple optical sources that emit light at a plurality of wavelengths and that are arranged from the perspective of a light detector as a point source.

In an embodiment, a non-invasive device is capable of producing a signal responsive to light attenuated by tissue at a measurement site. The device may comprise an optical source (made up of a plurality of light sources such as LEDs/SLEDs/Lasers within a 3 mm area) and one or a plurality of photodetectors. The one or plurality of photodetectors can be configured to detect the optical radiation from the optical source after attenuation by the tissue of the measurement site. The one or plurality of photodetectors also output a respective signal stream responsive to the detected optical radiation.

Certain embodiments of the present disclosure are configured to perform high speed spectral sweep analysis of the tissue being measured to non-invasively predict a patient's analyte levels, such as by way of non-limiting example, glucose levels. Informative spectral data can be obtained during the sweeping of specific wavelength regions of a patient's sample tissue. In previous configurations the spectral measurements are sensitive to sources of error, such as for example, fluctuations in the emitter (e.g., LED, SLED, and laser) power and temperature which can produce changes in the wavelength of emitted light. Rather than attempting to eliminate, to control, or to compensate for these sources of potential error, the present disclosure provides a system that uses these sources of fluctuation in the wavelength of the emitted light to its advantage. This sensitivity can be used advantageously to generate spectral sweeps over multiple wavelengths, by intentionally allowing the emitter temperature and/or the power to change. Accordingly, systems, devices and methods disclosed herein are used to monitor, control and/or adjust for, among other things, variations in emitter light source(s), emitter temperature(s), tissue temperature(s), and photodetector temperature(s) in order to use these sources to enhance the measurement process and reduce or eliminate unexpected or unwanted distortion in the collected spectral information that is reflective of blood and/or interstitial fluid constituents, such as, for example, glucose.

In an embodiment, the emitter is configured to receive a drive signal controlled by the processor. The drive signal comprises a drive current and a duty cycle, and the processor is configured to control the drive current and duty cycle. The drive current per cycle does not necessarily have a constant value, but rather, it can change in a controlled manner during a cycle such as, for example, linearly or logarithmically. Variation of the drive current and/or duty cycle can cause the emitter to emit light at varying wavelengths and powers. In some embodiments, a thermal controller is thermally coupled to the emitter to monitor and/or control the temperature of the emitter. The emitter is in thermal communication with the thermal controller which may include a temperature sensor, a thermoelectric cooler (such as, for example, a Peltier device), and a heat sink. The thermal controller is configured to receive a control signal from the processor and in response to such signal, adjust the operational temperature of the emitter to cause the emitter to emit light at varying wavelengths.

In some embodiments, data is collected at a high sampling rate (high speed) to obtain a larger quantity of spectral information than what can be collected using lower speed, averaged data collection methods. In some embodiments, tissue optical volume is controlled by fixing the distance between the emitter(s) and detector(s) and by ensuring that the sample tissue fills the fixed distance for each measurement. The sample tissue being measured contains, among other things, accumulated interstitial fluid which possesses metabolic levels of blood constituents, such as glucose, in concentrations similar to that found in blood. The sample tissue size and volume is controlled to reduce distortion and to increase the quantity of useful spectral information collected. Accurate measurement and/or control of emitter temperature, tissue sample temperature, and photodetector temperature are obtained to help secure the collection of valuable and useful spectral information reflective of blood and/or interstitial fluid constituents, such as glucose.

In some embodiments, control of the environment in which data is collected is maintained to reduce or eliminate sources of measurement variation. Illustratively, the temperature of the sample tissue may be measured to account for thermal fluctuations in the sample tissue which may affect the sensor measurements. Additionally, the temperature of the sample tissue may be controlled, by using, for example, a thermal controller or a thermoelectric cooler, to maintain the sample tissue at a constant temperature. In addition or alternatively, parts of the sensor may be controlled to match the sample tissue temperature measured.

In certain embodiments, the temperature of the detector(s) is measured by, for example, a temperature sensor, to account for thermal fluctuations in the detector(s) and to compensate for such fluctuations in the processing of the obtained measurements. In some embodiments, a thermoelectric cooler may be used to maintain the detector(s) at a constant temperature.

According to an embodiment, an optical physiological measurement system comprises an emitter configured to emit light at a plurality of wavelengths. The system includes a splitter configured to receive the emitted light and split it into a main (or primary, or first) beam and a set (or plurality) of auxiliary beams such as second beam, third beam etc. The system also includes a set (or plurality) of detectors. The first (or main) set of detectors is configured to detect the first (or main) beam of transmitted light after the first (or main) beam has been attenuated by a sample tissue being measured at a measuring site. The first set of detectors outputs a first signal responsive to the transmitted light of the first beam attenuated by the sample tissue at two different pathlengths. The system includes a second detector configured to detect the second beam of transmitted light and to output a second signal responsive to the detected light of the second beam. The second beam is attenuated by an absorber with flat spectral response; hence the second detector outputs a second signal proportional to the bulk emitted light, which characterizes its emitted power. The system includes a third detector configured to detect the third beam of emitted light after the third beam has been attenuated by a reference absorption material installed inside the system. The third detector outputs a third signal responsive to the detected light of the third beam attenuated by the reference absorption material at a desired spectral profile, which characterizes its emitted spectra. Alternatively the beam splitter may have additional auxiliary beams directed to additional absorption filters with diverse spectral responses in order to excite additional detectors responsive to the desired additional spectra. The system also includes a processor configured to receive signals responsive to the first (or main) and all other auxiliary signals to determine a bulk absorbance of an analyte in the sample tissue.

According to an embodiment, the system includes a splitter configured to receive and split the emitted light from said light source(s) into a plurality of beams (a first beam, a second beam, a third beam and a forth beam). The split beams are ideally equivalent to one another, with only a power scaling factor being the difference between any two beams. The spectral content of each beam shall be the same. The system also includes a first detector set configured to detect the first beam of emitted light after the first beam has been attenuated by a sample tissue being measured at a measuring site at two different paths through the tissue. The first detector outputs signals responsive to the detected light of the first beam through the two different paths of tissue. The system includes a second detector configured to detect the second beam of emitted light and to output a second signal responsive to the detected light of the second beam. The system includes a third detector configured to detect the third beam of emitted light after the third beam has been attenuated by a reference absorption material installed inside the system. The third detector outputs a third signal responsive to the detected light of the third beam. The system includes a fourth detector configured to detect the fourth beam of emitted light after the fourth beam has been attenuated by a second reference absorption material or other absorption material with known absorbance installed inside the system. The fourth detector outputs a fourth signal responsive to the detected light of the fourth beam. The system also includes a processor configured to receive signals responsive to the first, second, third and fourth signals to determine a bulk absorbance of an analyte in the sample tissue.

According to an embodiment, a high speed data collection device is used to receive and convert the first, the second, the third, the forth and any other desired output signals from an analog form to a digital form. The high speed data collection device includes a successive approximation register (SAR) analog-to-digital converter (ADC) to convert the plurality of detected signals from an analog form to a digital form for further processing.

In an embodiment, a tissue restriction apparatus, including an enclosure to receive the sample tissue, is used to control a distance between the emitter and the first detector. The tissue restriction apparatus may include a vacuum device configured to accumulate the sample tissue within the tissue restriction device. The tissue restriction device may also be configured to apply a pressure force to be distributed along the sample tissue within the enclosure. Illustratively, by way of non-limiting example, the tissue restriction apparatus can include a spring that is configured to apply pressure to the sample tissue at the measurement site to cause the sample tissue to be distributed substantially evenly throughout the measurement site. In some embodiments, the spring is controllable to enable adjustment of the applied pressure to the sample tissue so as to avoid the potential for occlusion of blood and/or interstitial fluid within the sample tissue. A tissue water volume within the measurement site may also be measured or estimated and used to compensate for differences between different tissue types. Different tissues have different compositions, and therefore the amount of water in the tissue from one location or subject to another will change. An estimation of this volume may be determined based on age, gender, or other demographic information, or it may also be estimated through a pressure measurement.

According to an embodiment, a method of varying light emitted in a physiological sensor includes determining a temperature, a drive current, a forward voltage and a duty cycle. It is to be understood that each of these variables (temperature, drive current, forward voltage and duty cycle)

may not need to be controlled to a constant value. Instead, each of these variables can be varied during measurement to achieve the purpose of varying the shape of light emitted in order to get the most information from the site. The method includes measuring a first indication of a physiological parameter. The method also includes altering at least one of the determined temperature, drive current, forward voltage, duty cycle, and shape of the emitter at a second time to cause the emitter to emit light at a second wavelength. The method further includes measuring a second indication of a physiological parameter. This method can be repeated as needed using different combinations of the variables to measure different indication(s) of a physiological parameter. Altering the determined temperature of the emitter can include using a circuitry-based temperature alteration device, which may include a Peltier device. Alternatively, the necessary temperature change can be obtained through the natural heat generated at the emitter device by the driving current and duty cycle according to the Joule's laws. In yet another embodiment, temperature control can be achieved passively using coupling fluid heated remotely to the desired temperature. In this embodiment, the fluid is dispensed to the measurement site area just prior to measurement and the site is brought into thermal equilibrium prior to measurement.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers can be re-used to indicate correspondence between referenced elements. The drawings are provided to illustrate embodiments of the inventions described herein and not to limit the scope thereof.

DETAILED DESCRIPTION

Figure 1:
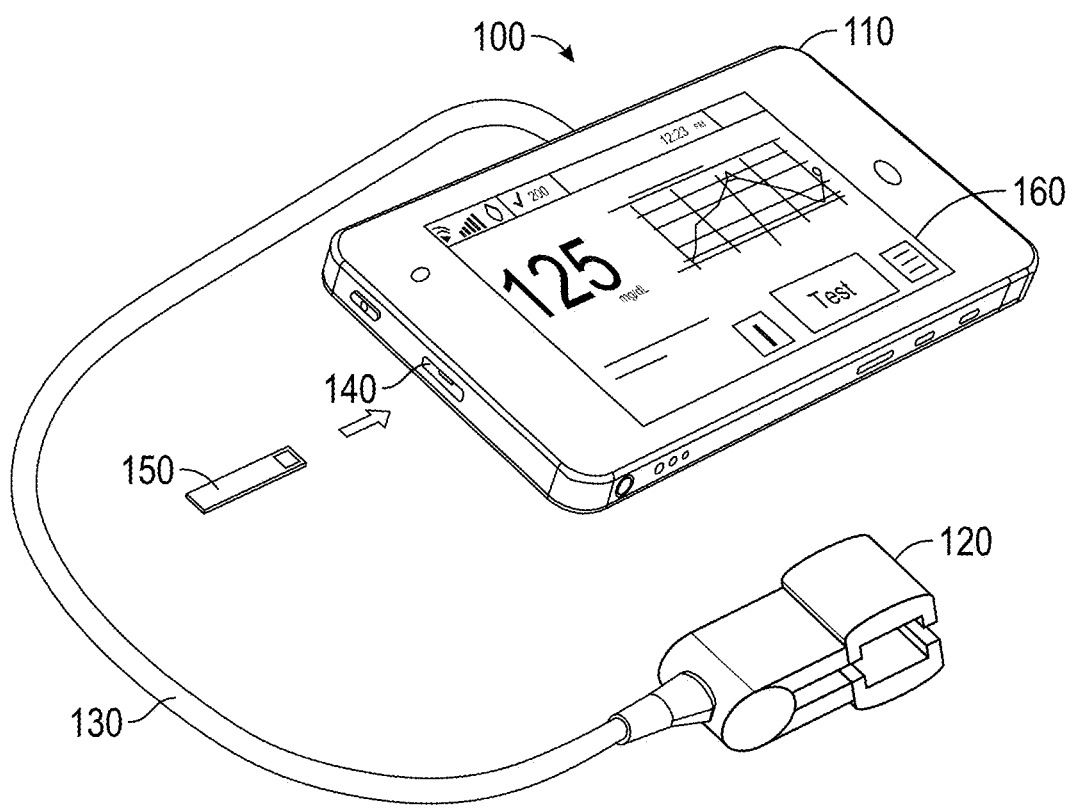
FIG. 1 illustrates an embodiment of a physiological measurement system for non-invasively and invasively measuring blood analytes.

FIG. 1 illustrates an embodiment of a monitoring system 100 that advantageously provides relatively frequent non-invasive measurements of a blood and/or interstitial fluid parameter, such as, for example, glucose, interspersed with relatively infrequent invasive measurements of the parameter. The monitoring system 100 is capable of communicating with networks, such as by way of non-limiting examples, the Internet, a wide-area network, or a local-area network, via a cellular component, a Wi-Fi connection, a Bluetooth interface, or the like. The monitoring system 100 has a monitor 110, an optical sensor 120, a sensor cable 130 electrically and mechanically interconnecting the monitor 110 and sensor 120, and an optional monitor-integrated test strip reader that accepts test strips 150 via a test strip slot 140. In an embodiment, the test strip reader measures blood glucose levels. In an embodiment, the monitoring system 100 individually calibrates the non-invasive optical sensor 120 measurements with intermittent test strip measurements to advantageously provide the accuracy of individualized test strip measurements at a much-reduced frequency of blood draws. Reduced blood draws is a substantial aid to persons who require frequent monitoring, for example in the case of monitoring blood glucose levels, to manage diabetes and related diseases. In an embodiment, the monitor 110 has a handheld housing including an integrated touch screen, or display 160 defining one or more input keys and providing a display of blood glucose levels among other features.

An optical sensor is described in detail with respect to U.S. patent application Ser. No. 13/646,659 titled Non-invasive Patient Assessment System and filed Oct. 5, 2012. A blood glucose monitor is described in detail with respect to U.S. patent application Ser. No. 13/308,461 titled Handheld Processing Device Including Medical Applications for Minimally and Non-invasive Glucose Measurements and filed Nov. 30, 2011. Blood glucose monitors and sensors are described in detail with respect to U.S. patent application Ser. No. 13/449,307, titled Blood Analysis System, filed Apr. 17, 2012 and U.S. patent application Ser. No. 13/473,477, titled Personal Health Device, filed May 16, 2012. A blood glucose calibration system is described in detail with respect to U.S. patent application Ser. No. 13/726,539 titled Blood Glucose Calibration System and filed Dec. 24, 2012. All of the above referenced patent applications are assigned to Cercacor and incorporated by reference herein in their entireties.

The monitor 110 can advantageously include electronic processing, signal processing, and data storage devices capable of receiving signal data from the sensor 120, processing the signal data to determine one or more output measurement values indicative of one or more physiological parameters of a monitored patient, and displaying the measurement values, trends of the measurement values, combinations of measurement values, and the like.

The cable 130 connecting the sensor 120 and the monitor 110 can be implemented using one or more wires, optical fiber, flex circuits, or the like. In some embodiments, the cable 130 can employ twisted pairs of conductors in order to minimize or reduce cross-talk of data transmitted from the sensor 120 to the monitor 110. Various lengths of the cable 130 can be employed to allow for separation between the sensor 120 and the monitor 110. The cable 130 can be fitted with a connector (male or female) on either end of the cable 130 so that the sensor 120 and the monitor 110 can be connected and disconnected from each other. Alternatively, the sensor 120 and the monitor 110 can be coupled together via a wireless communication link, such as an infrared link, radio frequency channel, or any other wireless communication protocol and channel.

The monitor 110 can be attached to the patient. For example, the monitor 110 can include a belt clip or straps that facilitate attachment to a patient's belt, arm, leg, or the like. The monitor 110 can also include a fitting, slot, magnet, snap-click connector, or other connecting mechanism to allow the cable 130 and sensor 120 to be attached to the monitor 110.

The monitor 110 can also include other components, such as a speaker, power button, removable storage or memory (e.g., a flash card slot), an AC power port, and one or more network interfaces, such as a universal serial bus interface or an Ethernet port. For example, the monitor 110 can include a display 160 that can indicate a measurement of glucose, for example, in mg/dL. Other analytes and forms of display can also appear on the monitor 110.

In addition, although a single sensor 120 with a single monitor 110 is shown, different combinations of sensors and device pairings can be implemented. For example, multiple sensors can be provided for a plurality of differing patient types or measurement sites.

In an alternative embodiment, the monitor 110 does not include a display or test strip reader. In such an embodiment, the monitor 110 is configured to wirelessly communicate with a user device, such as a smartphone. Alternatively the monitor can wirelessly communicate with a cloud-based computing network to upload data, download parameters, and post-process collected data if advantageously recommended or necessary. Measurements obtained by the monitor 110 are wirelessly communicated to the user device which is configured to receive and display the measurements and provide feedback to the user.

Figure 2:
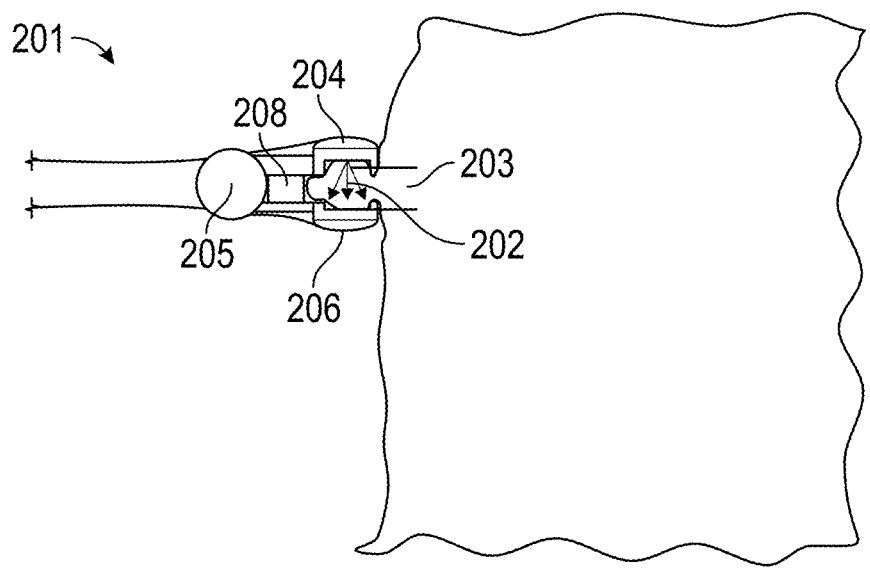
FIG. 2 illustrates a side view of an embodiment of a non-invasive sensor housing configured to measure a skin-fold pinch having a fixed distance between emitter(s) and detectors(s).

FIG. 2 illustrates an embodiment of the non-invasive optical sensor 120 of FIG. 1. The sensor 201 in the depicted embodiment is a hinged-clip type sensor that includes an enclosure 203 for receiving a skin-fold pinch (i.e., sample tissue) 202 of a patient. The enclosure 203 is formed by an upper section or emitter shell 204, which is pivotably connected with a lower section or detector shell 206. The emitter shell 204 can be biased with the detector shell 206 to close together around a pivot point 205 and thereby enclose sample tissue between the emitter and detector shells 204, 206 at a measurement site.

In an embodiment, the pivot point 205 advantageously includes a pivot capable of adjusting the relationship between the emitter and detector shells 204, 206 to apply appropriate pressure to the skin-fold pinch 202 of the measurement site. In another embodiment, the sensor 201 includes a spring (not shown) that causes the pressure force to be distributed along the sample tissue 202. The sensor includes a depth stop 208 which serves to define a fixed distance between the emitter shell 204 and the detector shell 206, thereby defining a known path length between emitter(s) and detector(s).

The pressure exerted by the spring can be controllably variable. In an embodiment, the spring pressure exerted on the skin-fold pinch 202 is taken into account during calculation of the measurement. For example, measurements taken by the optical sensor 201 are sensitive to pressure. The greater the pressure that is exerted on the skin-fold pinch 202, the smaller the potential measured signal (which may also be referred to as plethysmograph) becomes. With sufficient pressure, the sample tissue 202 can be occluded, and no plethysmograph will be detected. Spring pressure can also affect the shape of the plethysmograph and the physiological composition of the material affected by the pulse wave that generates the plethysmograph. For example, during glucose measurements, pressure applied by the spring can force glucose out and away from the sample tissue 202 in the measurement site. Thus, during measurement, a known spring pressure or effect on the sample tissue 202 in the measurement site can be taken into account to adjust the determined measurements. In some embodiments, spring pressure is predetermined at manufacture and encoded onto a memory device (not shown) in of the sensor 201. In some embodiments, a pressure sensor or other type of sensor is used on the sensor 201 to determine a current pressure exerted by the spring. In some embodiments, a general estimate or compensation for spring pressure is used without measuring or otherwise determining specific spring pressure effects by each individual sensor 201.

The emitter shell 204 can position and house various emitter components of the sensor 201. It can be constructed of reflective material (e.g., white silicone or plastic) and/or can be metallic or include metalized plastic (e.g., including carbon and aluminum) to possibly serve as a heat sink. The emitter shell 204 can also include absorbing opaque material, such as, for example, black or grey colored material, at various areas, such as on one or more flaps (not shown), to reduce access of ambient light entering the measurement site and the sensor 201.

The detector shell 206 can position and house one or more detector portions of the sensor 201. The detector shell 206 can be constructed of reflective material, such as white silicone or plastic. Such materials can increase the usable signal at a detector by forcing light back into the tissue and measurement site. The detector shell 206 can also include absorbing opaque material at various areas (not shown) to reduce ambient light entering the measurement site and the sensor 201. The opaque material of the detector shell 206 may also serve the purpose of reducing light piping from the emitter 204 to the detector 206 and force all the light from the emitter to pass through the tissue sample.

Care may be taken when physically coupling the surface of the skin 202 to the surface of the emitter shell 204 or detector shell 206. In some embodiments a tissue shaper in the form of a cavity 203 is provided to permit the tissue sample to fill the space in an evenly distributed manner, without overlap of sample tissue 202. In some embodiments a vacuum chamber (not shown) is used to help distribute the sample tissue 202 appropriately. The vacuum chamber can also provide a controlled amount of suction pressure to help achieve a proper distribution of blood and/or interstitial fluid within the sample tissue 202.

In certain embodiments, the optical properties of the sample tissue 202 can be stabilized by application of a coupling agent, such as, by way of non-limiting example, a perfluorinated liquid. One such perfluorinated liquid is known by the brand name Fluorinert™, manufactured by 3M Company, of St. Paul, Minnesota. A coupling agent reduces variations in surface reflection of the sample tissue 202, thereby improving accuracy of the non-invasive measurement of the sample tissue 202. An additional feature of the coupling agent is that it may provide temperature stabilization of the sample tissue 202.

Figure 11:
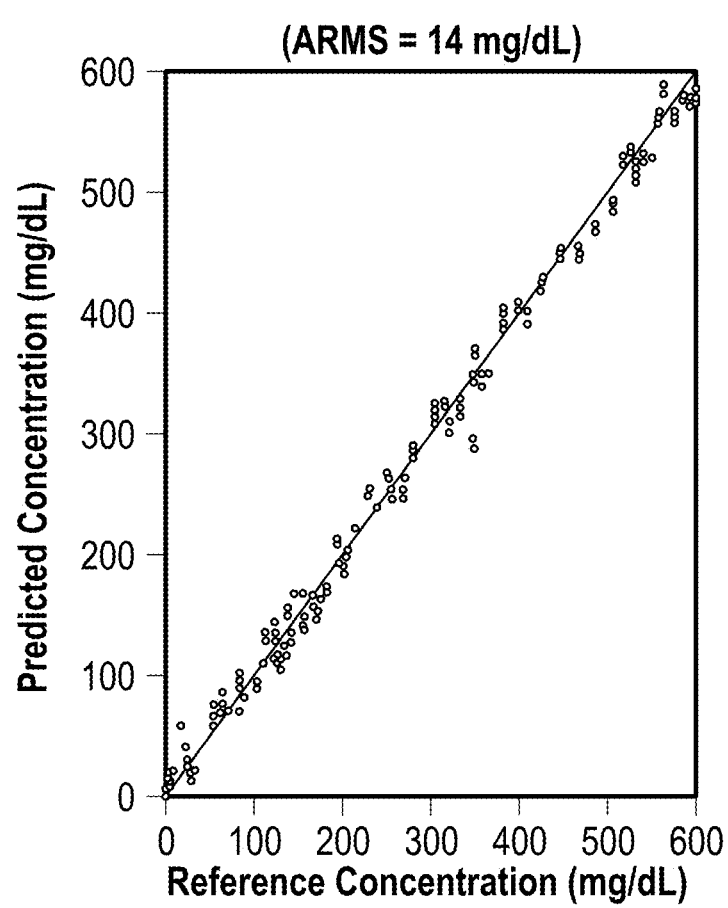
FIG. 11 illustrates correlation between a reference concentration of glucose in sample solutions and a predicted concentration of glucose as determined by the disclosed high speed spectral sweep analysis system.
Figure 12:
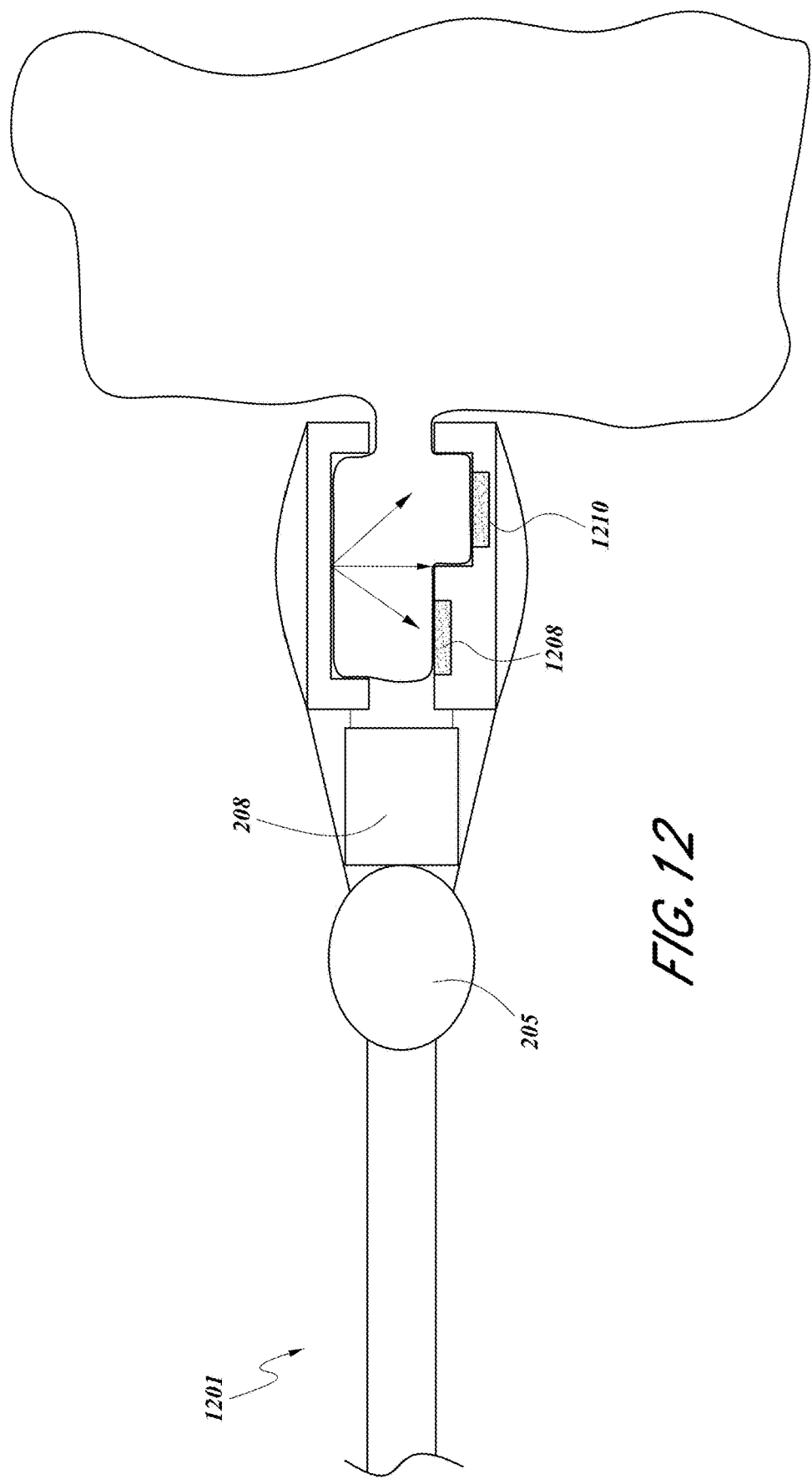
FIG. 12 illustrates the sensor from FIG. 1 and FIG. 2 that has two different photodiodes sampling light from two different paths through the tissue.

FIG. 12 illustrates an embodiment of the non-invasive optical sensor 120 of FIG. 1. The sensor 120 is similar to that described in FIG. 2 with the difference that FIG. 12 illustrates an embodiment with multiple photodiodes channels. The two photodiode channels, 1208, 1210 are located at different heights from the emitters such that when the tissue fills the space between the emitter and detector it will create two distinct light paths that have different lengths. The height difference for the two photodiodes can be optimized at a height that doesn't stretch the skin too much, but allows for a maximum difference in heights. Stretching of the skin can cause scattering changes in the tissue which effects the optical signal detected. The ideal height difference would create minimal stretching in the skin, not have scattering transients during sensor placement and be repeatable for multiple sensor placements. The height difference between detectors would preferably be between 0.2 mm and 1 mm. The step between the two photodiode heights could be a right angle, but in a some embodiments it can be a 45 degree angle with rounded corners in order for the skin in the tissue sample to not get caught on a sharp edge. Other embodiments could include more of a curved surface than a straight surface. FIG. 12 depicts the two photodiodes 1208 and 1210 running from back to front of the sensor, but some embodiments can have the two photodiodes run transverse to the sensor head such that they both see similar parts of tissue. All other embodiments described for the sensor in FIG. 2 can still apply to the senor in FIG. 11.

Figure 3:
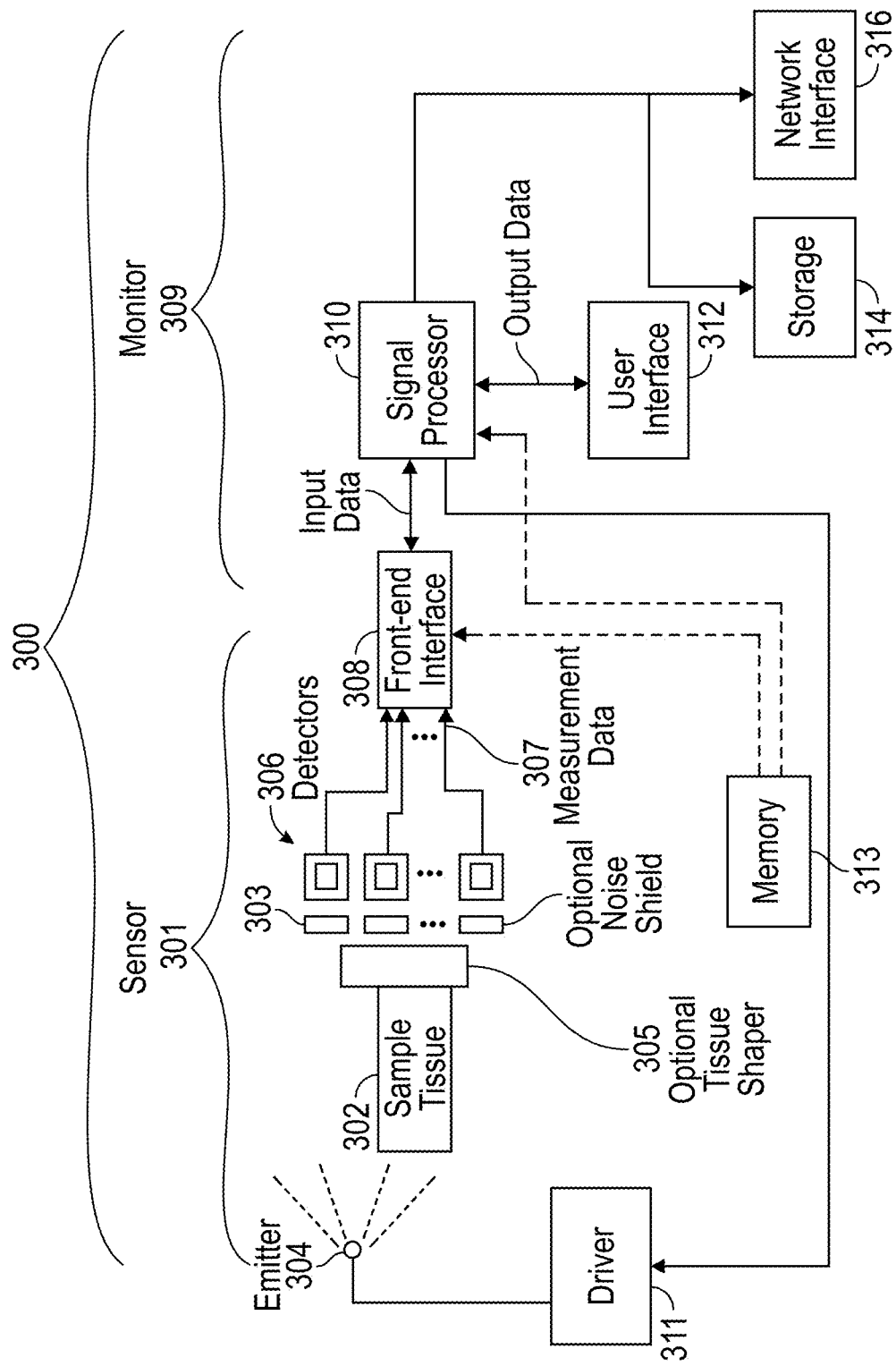
FIG. 3 illustrates a block diagram of an embodiment of a physiological measurements system.

FIG. 3 illustrates an example of a data collection system 300, which can be embodied in the devices of FIGS. 1-2 and 12. In certain embodiments, the data collection system 300 non-invasively measures a blood and/or interstitial fluid analyte, such as oxygen, carboxyhemoglobin, met-hemoglobin, total hemoglobin, glucose, proteins, lipids, a percentage thereof (e.g., saturation) or for measuring many other physiologically relevant patient characteristics, including other characteristics described herein. The system 300 can also measure additional blood and/or interstitial fluid analytes and/or other physiological parameters useful in determining a physiological state or trend of wellness of a patient.

The data collection system 300 can be capable of measuring optical radiation from the measurement site. For example, in some embodiments, the data collection system 300 can employ photodiodes defined in terms of area. In an embodiment, the area is from about 0.25 mm$^2$-5 mm$^2$ (or higher) that is capable of detecting about 100 nanoamps (nA) or less of current resulting from measured light at full scale. In addition to having its ordinary meaning, the phrase "at full scale" can mean light saturation of a photodiode amplifier (not shown) or the voltage swing across a region of the circuitry that is defined by its linear region within the limits of electrical analog and digital saturation. Of course, as would be understood by a person of skill in the art from the present disclosure, various other sizes and types of photodiodes can be used with the embodiments of the present disclosure with diverse capability of current detection.

The data collection system 300 can measure a range of approximately about 1 nA to about 1000 nA full scale. The data collection system 300 can also include sensor front-ends that are capable of processing and amplifying current from the detector(s) at signal-to-noise ratios (SNRs) of about 100 decibels (dB) or more, such as about 120 dB in order provide sufficient signal quality to measure various desired analytes. The data collection system 300 can operate with a lower SNR if less accuracy and/or precision is desired for an analyte like glucose.

The data collection system 300 can measure analyte concentrations, including glucose, at least in part by detecting light attenuated by sample tissue 302 at a measurement site. The sample tissue 302 can be at any location on a patient's body, such as a skin-fold pinch, the patient's purlicue (skin web between the thumb and index finger), ear lobe, nasal septum, finger, foot, or the like.

In the depicted embodiment, the system 300 includes an optional tissue thickness adjuster or tissue shaper 305, which can include one or more protrusions, bumps, lenses, vacuums, or other suitable tissue-shaping mechanisms. In certain embodiments, the tissue shaper 305 is a flat or substantially flat surface that can be positioned proximate the sample tissue 302 at the measurement site and that can apply sufficient pressure to cause the sample tissue 302 to be flat or substantially flat. In other embodiments, the tissue shaper 305 is a convex or substantially convex surface with respect to the measurement site. Many other configurations of the tissue shaper 305 are possible. Advantageously, in certain embodiments, the tissue shaper 305 reduces thickness of the sample tissue 302 at the measurement site while preventing or reducing occlusion. Reducing thickness of the sample tissue 302 can advantageously reduce the amount of attenuation of the emitted light because there is less tissue through which the light must travel. Shaping the tissue into a convex (or alternatively concave) surface can also provide more surface area from which light can be detected.

The embodiment of the data collection system 300 shown also includes an optional noise shield 303. In an embodiment, the noise shield 303 can be advantageously adapted to reduce electromagnetic noise while increasing the transmittance of light from the sample tissue 302 to one or more detector(s) 306 (described below).

The data collection system 300 can include a sensor 301 (or multiple sensors) that is coupled to a processing device or physiological monitor 309. In an embodiment, the sensor 301 and the monitor 309 are integrated together into a single unit. In another embodiment, the sensor 301 and the monitor 309 are separate from each other and communicate with one another in any suitable manner, such as via a wired or wireless connection. The sensor 301 and monitor 309 can be attachable and detachable from each other for the convenience of the user or caregiver, for ease of storage, for sterility issues, or the like. The sensor 301 and the monitor 309 will now be further described.

In the depicted embodiment shown in FIG. 3, the sensor 301 includes one or more emitters at a single or multiple locations 304, a tissue shaper 305, one or more detector(s) at a single or multiple locations 306, and a front-end interface 308. The emitters 304 can serve as the source of optical radiation transmitted towards a measurement site 302. As will be described in further detail below, the emitters 304 can include one or more sources of optical radiation, such as LEDs (including, by way of non-limiting example, top-emitting LEDs, side-emitting LEDs, super-luminescent LEDs), laser diodes, incandescent bulbs with appropriate frequency-selective filters, combinations of the same, or the like. In an embodiment, the emitters 304 include sets of optical sources that are capable of emitting visible and near-infrared optical radiation.

In some embodiments, the emitters 304 are used as a point optical source, and thus, the one or more optical sources of the emitters 304 can be located within a close distance to each other, such as within about 2 mm to about 4 mm from each other. The emitters 304 can be arranged in an array, such as is described in U.S. Publication No. 2006/0211924, filed Sep. 21, 2006, titled "Multiple Wavelength Sensor Emitters," the disclosure of which is hereby incorporated by reference in its entirety. In particular, the emitters 304 can be arranged at least in part as described in paragraphs [006] through [0068] of the aforementioned publication, which paragraphs are hereby incorporated specifically by reference. Other relative spatial relationships can be used to arrange the emitters 304.

The emitters 304 of the data collection system 300 can emit, in certain embodiments, combinations of optical radiation in various bands of interest. For example, in some embodiments, for analytes like glucose, the emitters 304 can emit optical radiation at three (3) or more wavelengths between about 1330 nm to about 1660 nm. Depending on the available technology of optical emitters and detectors, wavelength values up to 1700 nm or even 1800 nm can be used to improve the accuracy of an analyte. In particular, the emitters 304 can emit optical radiation at or about 1370 nm, about 1540 nm, about 1585 nm, and about 1610 nm. In some circumstances, the use of three wavelengths within about 1540 nm to about 1610 nm enables sufficient SNRs of about 100 dB, which can result in a measurement accuracy of about 10 mg/dL or better for analytes like glucose.

In other embodiments, the emitters 304 can use two (2) wavelengths within about 1540 nm to about 1610 nm, which can result in a measurement accuracy of about 20 mg/dL or better for analytes like glucose. Furthermore, in some embodiments, the emitters 304 can emit light at wavelengths above about 1670 nm. Measurements at these wavelengths can be advantageously used to compensate for or confirm the contribution of protein, water, and other non-hemoglobin species exhibited in measurements for analytes like glucose conducted between about 1540 nm and about 1610 nm. Of course, other wavelengths and combinations of wavelengths can be used to measure analytes and/or to distinguish other types of tissue, fluids, tissue properties, fluid properties, combinations of the same, or the like.

For example, the emitters 304 can emit optical radiation across other spectra for other analytes. In particular, the emitters 304 can employ light wavelengths to measure various blood analytes or percentages (e.g., saturation) thereof. For example, in one embodiment, the emitters 304 can emit optical radiation in the form of pulses at wavelengths about 905 nm, about 1050 nm, about 1200 nm, about 1300 nm, about 1330 nm, about 1610 nm, about 1640 nm, and about 1665 nm. In another embodiment, the emitters 304 can emit optical radiation ranging from about 860 nm to about 950 nm, about 950 nm to about 1100 nm, about 1100 nm to about 1270 nm, about 1250 nm to about 1350 nm, about 1300 nm to about 1360 nm, and about 1590 nm to about 1700 nm. Of course, the emitters 304 can transmit any of a variety or combination of wavelengths of ultra-violet, visible and near-infrared optical radiation.

Due to the different responses of analytes to the different wavelengths, certain embodiments of the data collection system 300 can advantageously use the measurements at these different wavelengths to improve the accuracy of measurements. For example, the measurements of water from visible and infrared light can be used to compensate for water absorbance that is exhibited in the near-infrared wavelengths.

As briefly described above, the emitters 304 can include sets of light-emitting diodes (LEDs) as their optical source. The emitters 304 can use one or more top-emitting LEDs. In particular, in some embodiments, the emitters 304 can include top-emitting LEDs emitting light at about 850 nm to 1350 nm. The emitters 304 can also use super-luminescent LEDs (SLEDs) or side-emitting LEDs. In some embodiments, the emitters 304 can employ SLEDs or side-emitting LEDs to emit optical radiation at about 1300 nm to about 1800 nm. Emitters 304 can use SLEDs or side-emitting LEDs to transmit near infrared optical radiation because these types of sources can transmit at high power or relatively high power, e.g., about 40 mW to about 150 mW. This higher power capability can be useful to compensate for or to overcome the greater attenuation of these wavelengths of light in tissue and water.

The data collection system 300 also includes a driver 311 that drives the emitters 304. The driver 311 can be a circuit or the like that is controlled by the monitor 309. For example, the driver 311 can provide pulses of current to the emitter 304. In an embodiment, the driver 311 drives the emitters 304 in a progressive fashion, such as in an alternating manner. The driver 311 can drive the emitters 304 with a series of pulses of about 1 milliwatt (mW) for some wavelengths that can penetrate tissue relatively well, and from about 40 mW to about 150 mW for other wavelengths that tend to be significantly absorbed in tissue. In an embodiment, an array of drivers can be used to drive multiple emitters at the same time at different duty cycles, different frequencies, and various current drives. As mentioned above, the current does not have to be a pulse or a series of pulses. For example a linear ramping, logarithmic or exponential current can be selected as the drive current during the cycles. A skilled artisan will appreciate that a wide variety of other driving powers and driving methodologies can be used in various embodiments.

The detector(s) 306 capture and measure light attenuated (or reflected) by the sample tissue 302 at the measurement site. For example, the detector(s) 306 can capture and measure light transmitted from the emitters 304 that has been attenuated or reflected from the sample tissue 302 in the measurement site. The detector(s) 306 can output a detector signal (which may also be referred to as measurement data) 307 responsive to the light captured or measured. The detector(s) 306 can be implemented using one or more photodiodes, phototransistors, or the like. The detector(s) can be placed within a defined location or sparsely placed over many locations. In an embodiment, the detector can include capabilities to detect light which is both transmitted through the tissue and reflected from the tissue. In an embodiment, the system uses measurements from both the transmitted and/or reflected light in the determination of physiological parameters. The system can also make a determination of which signal (transmitted through or reflected) provides the best signal and use that signal. Alternatively or in addition, the system can make a quality of signal determination for each of the transmitted through or reflected signals and use the quality information to weight the signals in order to determine a combined signal. The quality determination and combining of the signals can be performed at startup or throughout the measurement process.

The front end interface 308 provides an interface that adapts or conditions the output of the detector(s) 306, which is responsive to desired physiological parameters. For example, the front end interface 308 can adapt or condition a detector signal 307 received from one or more of the detector(s) 306 into a form that can be processed by the monitor 309, for example, by a signal processor 310 in the monitor 309. The front end interface 308 can have its components assembled in the sensor 301, in the monitor 309, in the connecting cabling 130 (if used), in combinations of the same, or the like. The location of the front end interface 308 can be chosen based on various factors including space desired for components, desired noise reductions or limits, desired heat reductions or limits, and the like.

The front end interface 308 can be coupled to the detector(s) 306 and to the signal processor 310 using a bus, wire, electrical or optical cable, flex circuit, or some other form of signal connection. The front end interface 308 can also be at least partially integrated with various components, such as the detector(s) 306. For example, part of the front end interface can be built into the detector package while the remaining can be placed outside the detector package. The front end interface 308 can include one or more integrated circuits that are on the same circuit board as the detector(s) 306. Other configurations can also be used.

The front end interface 308 can be implemented using one or more amplifiers, such as transimpedance amplifiers (TIAs) that are coupled to one or more analog-to-digital converters (ADCs) (which can be in the monitor 309), such as a successive approximation register (SAR) ADC. A transimpedance-based front end interface 308 can employ single-ended circuitry, differential circuitry, and/or a hybrid configuration. A transimpedance-based front end interface 308 can be useful for its sampling rate capability and its freedom in modulation/demodulation algorithms. For example, this type of front end interface 308 can advantageously facilitate the sampling of the ADCs being synchronized with the pulses emitted from the emitters 304.

The ADC or ADCs can provide one or more outputs into multiple channels of digital information for processing by the signal processor 310 of the monitor 309. Each channel can correspond to a signal output from a detector 306.

In some embodiments, a programmable gain amplifier (PGA) can be used in combination with a transimpedance-based front end interface 308. For example, the output of a transimpedance-based front end interface 308 can be output to a PGA that is coupled with an ADC in the monitor 309. A PGA can be useful in order to provide another level of amplification and control of the stream of signals from the detector(s) 306. Alternatively, the PGA and ADC components can be integrated with the transimpedance-based front end interface 308 in the sensor 301.

In another embodiment, the front end interface 308 can be implemented using switched-capacitor circuits. A switched-capacitor-based front end interface 308 can be useful for, in certain embodiments, its resistor-free design and analog averaging properties. In addition, a switched-capacitor-based front end interface 308 can be useful because it can provide a digital signal to the signal processor 310 in the monitor 309.

As shown in FIG. 3, the monitor 309 can include the signal processor 310 and a user interface, such as a display 312. The monitor 309 can also include optional outputs alone or in combination with the display 312, such as a storage device 314 and a network interface 316. In an embodiment, the signal processor 310 includes processing logic that determines measurements for desired analytes, such as glucose, based on the signals received from the detector(s) 306. The signal processor 310 can be implemented using one or more microprocessors or subprocessors (e.g., cores), digital signal processors, application specific integrated circuits (ASICs), field programmable gate arrays (FPGAs), combinations of the same, and the like.

The signal processor 310 can provide various signals that control the operation of the sensor 301. For example, the signal processor 310 can provide emitter control signals to the driver 311. These control signals can be used to modulate the emitted wavelengths from the emitter(s) 304. As also shown, an optional memory 313 can be included in the front-end interface 308 and/or in the signal processor 310. This memory 313 can serve as a buffer or storage location for the front-end interface 308 and/or the signal processor 310, among other uses.

The user interface 312 can provide an output, e.g., on a display, for presentation to a user of the data collection system 300. The user interface 312 can be implemented as a touch-screen display, an LCD display, an organic LED display, or the like. In addition, the user interface 312 can be manipulated to allow for measurement on the non-dominant side of patient. For example, the user interface 312 can include a flip screen, a screen that can be moved from one side to another on the monitor 309, or can include an ability to reorient its display indicia responsive to user input or device orientation. In alternative embodiments, the data collection system 300 can be provided without a user interface 312 and can simply provide an output signal to a separate display or system.

A storage device 314 and a network interface 316 represent other optional output connections that can be included in the monitor 309. The storage device 314 can include any computer-readable medium, such as a memory device, hard disk storage, EEPROM, flash drive, or the like. The various software and/or firmware applications can be stored in the storage device 314, which can be executed by the signal processor 310 or another processor of the monitor 309. The network interface 316 can be a serial bus port (RS-232/RS-485), a Universal Serial Bus (USB) port, an Ethernet port, a wireless interface (e.g., Wi-Fi such as any 802.1x interface, including an internal wireless card), or other suitable communication device(s) that allows the monitor 309 to communicate and share data with other devices. The monitor 309 can also include various other components not shown, such as a microprocessor, graphics processor, or controller to output the user interface 312, to control data communications, to compute data trending, or to perform other operations.

Although not shown in the depicted embodiment, the data collection system 300 can include various other components or can be configured in different ways. For example, the sensor 301 can have both the emitter 304 and detector(s) 306 on the same side of the measurement site 302 and use reflectance to measure analytes. The data collection system 300 can also include a sensor that measures the power of light emitted from the emitter 304 by splitting the beam from the emitter 304 and directing to one of the photodiode channels 306 without passing the beam through the sample tissue 302. The data collection system 300 can also include a sensor that measures light that has passed through a reference material in order to track wavelength shifts in the emitter 304. Light that passes through the reference material will be attenuated in an known manner. Thus a change in wavelength will create a predictable change in real time. This will allow for real-time wavelength tracking that can be used to adjust for emitter variation and/or to determine whether the probe is accurate enough for use. One such reference material can be a cell filled with water. Another such reference material is didymium which has an absorption peak similar to water. Didymium's absorption peak is around 1490-1510 nm. If the reference material has an absorption that varies with temperature the temperature of the reference material can be monitored and used for compensation in an algorithm or the reference material can be controlled to a specified temperature.

Figure 4:
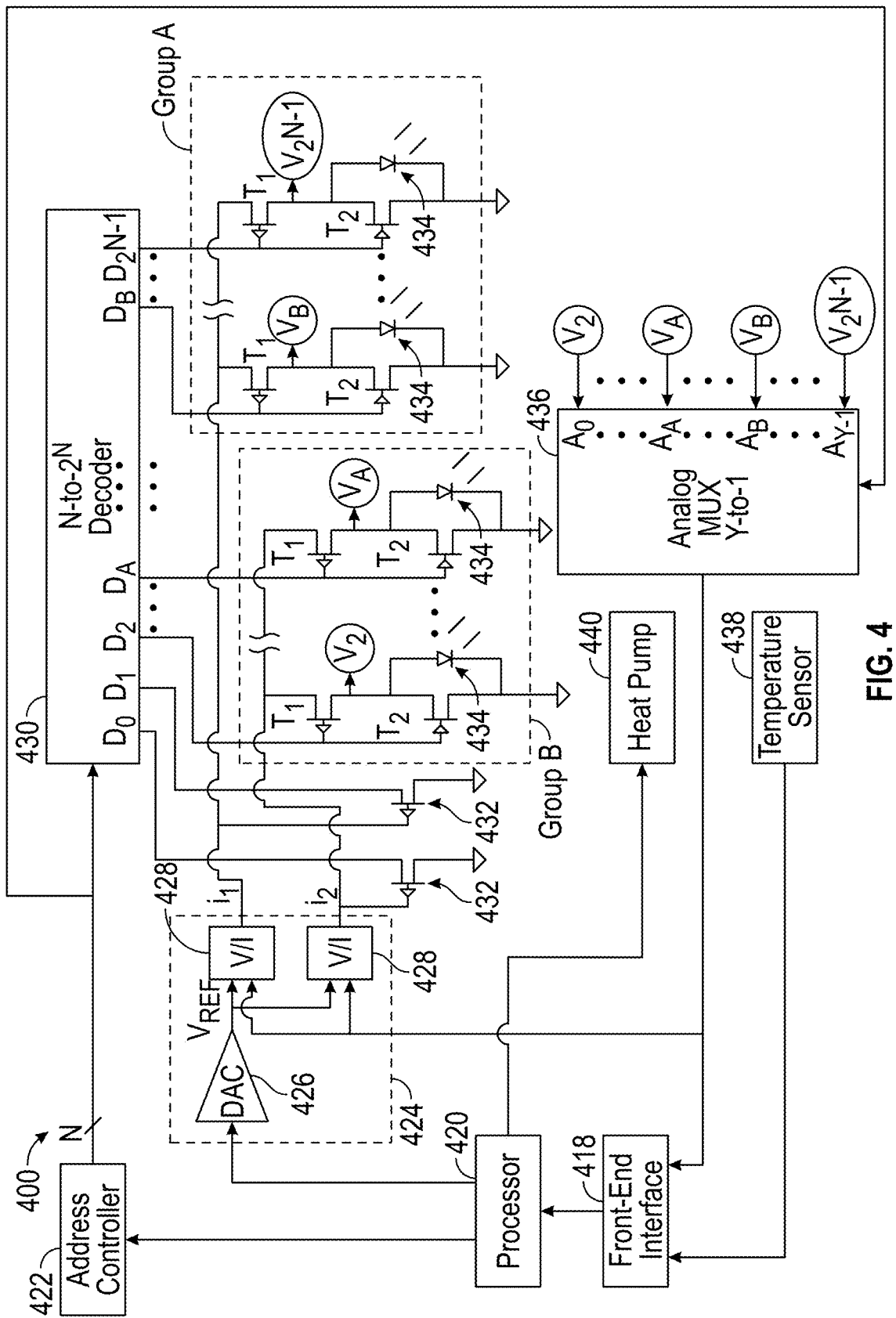
FIG. 4 illustrates a schematic diagram of the current driver of an embodiment of a patient monitoring system.

FIG. 4 illustrates a block diagram of an embodiment of the system 400 illustrating further details of the devices of FIGS. 1-3. The system 400 includes an address controller 422, a current controller 424, and an address decoder 430, among other components. The system 400 can function at least in part like one or more of the patient monitoring systems described in U.S. Pat. No. 8,688,183 (the '183 patent), such as with respect to at least FIGS. 4, 5, 7A, 7B, 8, and 9 of the '183 patent. The disclosure of the '183 patent is incorporated in its entirety by reference herein. In addition to the components of the patient monitoring systems described in the '183 patent, the system 400 includes an analog multiplexer (mux) 436.

The components of the system 400 can advantageously enable use of addressing and an analog multiplexing. The addressing information can be used, in part, to limit or reduce a number of conductors that may be required for transmitting signals from, for example, the sensor 120 or the cable 130 to the monitor 110. Accordingly, the potential of harmful crosstalk between conductors can be reduced as a result of fewer conductors. In addition, cables associated with the present disclosure may advantageously use fewer larger heavily shielded driver conductors, and therefore, may be less costly to produce and be less rigid or stiff and thus more ergonomic for a wearer of a sensor.

The address controller 422 and the current controller 424 can precisely control activation of the light source 434 in response to instructions (for instance, data, clock, and latch signals) from a processor 420. Such control circuitry can be used to perform, for example, high speed spectral sweep analysis as described in more detail below. The address controller 422 can output an address, such as, for example, a binary number, to the decoder 430 via N conductors. The decoder 430 can decode the address received via the N conductors and identify particular LED(s) of the light source 434 to be connected to the current controller 424. Once connected, current can flow through the particular LED, thereby activating it to irradiate tissue.

In an embodiment, one LED node may be energized at a time, and in further embodiments, time spacing or a gap can be provided between consecutive activations to guard against interference at the detector 306 by light of differing wavelengths. The gap, or no LED activation, can occur between activations of LEDs, and the gap can include one of the 2N addressable locations such that an all-off condition is specifically addressable by the processor 420.

The current controller 424 includes a digital-to-analog converter (DAC) 426 configured to convert digital signals from the processor 420 into analog output. The DAC 426 can control light saturation by allowing for the fine tuning of the output drive current. The DAC 426 can receive clock and data signals from the processor 420 and a latching signal dictating when the DAC should lock the data on the data signal and stabilize the output drive current.

The output of the DAC 426 is provided to a plurality of amplifiers 428 which, in an embodiment, can include precision voltage-to-current amplifiers (or trans-conductance amplifiers—TCA) that adjust output currents based on one or more input voltages. In this embodiment, the current controller 424 can output two different currents $i_1$ and $i_2$ via the plurality of amplifiers 428 according to, in some instances, the voltage output by the DAC 426 as well as an output signal from the analog mux 436. The output of the plurality of amplifiers 428 can, in turn, be provided as the driving current to the LEDs of the light source 434. FIG. 4 shows output current $i_1$ communicating with the nodes of a first group of LEDs, Group A, and the output current $i_2$ communicating with the nodes of a second group of LEDs, Group B. In one example, the output current $i_1$ may be about 0 to about 80 mA, while the output current $i_2$ may comprise about 0 to about 800 mA. An artisan will recognize that other embodiments may advantageously employ other currents and/or have more or less groups.

The address controller 422 can output the same address to the analog mux 436 via N conductors as was output to the decoder 430. The address controller 422 can, for instance, output an address to the decoder 430 and the analog mux 436 in parallel with one another or at substantially the same time. The analog mux 436 can use the address received via the N conductors to identify an input of multiple inputs of the analog mux 436 that is associated with the address. For example, a received binary set of N bits can be identified as associated with a particular input of the analog mux 436 according to a mapping. In response to receiving the address from the address controller 422, the analog mux 436 can connect the identified input of the analog mux 436 associated with the address to the output of the analog mux 436 to output a signal received via the identified input to the front-end interface 418 and the current controller 424.

The decoder 430 and the analog mux 436 can furthermore have a common one-to-one mapping for a particular address to a particular LED of the light source 434. When the decoder 430 may receive a particular address corresponding to activation of a particular LED of the light source 434, the analog mux 436 can map the same particular address to an input of the analog mux 436 that may be connected to the drain of the of the same particular LED. Thus, when the decoder 430 activates the particular LED of the light source 434, the analog mux 436 may function to pass the voltage associated with the activated LED to the front-end interface 418 and the current controller 424. For example, if the address controller 422 outputs an address which the decoder 430 decodes to correspond to the output $D_2$, the decoder 430 can activate the output $D_2$ so that the corresponding LED of the light source 434 irradiates. At substantially the same time, the analog mux 436 can receive the same address and accordingly connect the input $A_0$ to the output of the analog mux 436, so the analog mux 436 communicates the forward voltage $V_2$ of the irradiating LED to the front-end interface 418 and the plurality of amplifiers 428 of the current controller 424. Information of the forward voltage of an activated LED can advantageously help to enhance the algorithms used to calculate the irradiated power and irradiated wavelength spectra, which will further be used to improve the accuracy of the measured analyte.

Of course, those skilled in the art will appreciate that the aforementioned methodology can be expanded using multiple address decoders, DACs and analog muxes to allow the multiple driving of multiple emitters at the same time. Furthermore, the availability of FPGAs (Field Programmable Gate Arrays) is making it possible to integrate multiple address decoder functionality into a single part. Also, FPGAs may be programmed to provide multiple shape/waveform of currents for the emitters.

The system 400 additionally or alternatively includes a temperature sensor 438. The temperature sensor 438 can be used to measure the temperature near one or more of the LEDs of the light source 434 or for providing a measurement of the bulk temperature near the light source 434. The temperature sensor 438 can provide a temperature signal responsive to the measured temperature to the front-end interface 418. In an embodiment, the temperature sensor 438 can include multiple temperature sensors 436 positioned at different locations near the different LEDs of the light source 434. The particular temperature sensor 438 may be closer to an activated LED of the light source 434 than another temperature sensor 438 of the multiple temperature sensors 436 so that a more accurate temperature reading of the activated LED can be determined. The system can also include multiple temperature sensors to allow the temperature reading of the tissue sites, and detectors. Information of the temperature of an activated LED can advantageously help to enhance the algorithms used to correct for the irradiated power and irradiated wavelength spectra, which will further be used to improve the accuracy of the measured analyte.

The system 400 further includes a heat pump 440. The heat pump 440 can be placed near one or more of the LEDs of the light source 434 and controlled by the processor 420 to remove, to add, or to control the heat near the light source 434. The heat pump can also be used to control and change the temperature of the light source(s). In an embodiment, the heat pump 440 can be a Peltier pump or device. In another embodiment the heat pump 440 can be a passive heat sink. In another embodiment there could be no heat pump 440 in a case where it is desired for the temperature to sweep a large range in order to naturally sweep a large wavelength range. In an embodiment, the heat pump 440 can include multiple heat pumps disposed at different locations near the different LEDs of the light source 434. The particular heat pump may be closer to an activated LED of the light source 434 so that more heat near the activated LED of the light source 434 can be controlled than if another heat pump of the multiple heat pumps were activated. In another embodiment, the decoder 430 itself can additionally or alternatively be used to control the heat pump 440. Moreover, in some embodiments, one or more heat pumps can be disposed near one or more photodetectors 306 used to detect light irradiated by the light source 434.

The front-end interface 418 can filter and pre-process received signals and output filtered and processed signals to the processor 420. The front-end interface 418 may, for example, include one or more high-pass filters, analog line-drivers, programmable gain amplifiers (PGAs), analog-to-digital converters (ADCs), or the like for processing a voltage signal from the analog mux 436 or the temperature signal(s) from the temperature sensor(s) 438.

While the processor 420 may receive the output filtered and processed signals from the front-end interface 418, the processor 420 can use information from the received signals to control components of the system 400 and determine measurement values for one or more monitored parameters of a patient. In one example, the processor 420 can determine the forward voltage of an activated LED of the light source 434 to, for instance, control an emitted wavelength and power output of the activated LED. The processor 420 can also determine a temperature measured by the temperature sensor 438 to further refine this predicted centroid wavelength or wavelength distribution and power output of the activated LED. In addition, an estimated temperature of the activated LED can be compared, in some instances, to the temperature measured by the temperature sensor 438 to determine a difference between a bulk temperature and the temperature of the activated LED. The processor 420 can accordingly use this information to obtain more accurate and precise measurement values for the one or more monitored parameters. The relationships between an LED forward voltage, centroid wavelength, power output, junction temperature, duty cycle, and current are known to a skilled artisan and thus not described in herein. Example algorithms for determining measurement values can be found in U.S. Pat. No. 6,157,850 (the '850 patent). The disclosure relating to determination of measurements from sensor data in the disclosure of the '850 patent is incorporated in its entirety by reference herein.

The output signal from the analog mux 436 can, in some embodiments, be used to control the currents $i_1$ and $i_2$ to vary the centroid wavelength (for example, by ±15 nm from a rated centroid wavelength) of an LED of the light source 424 so that the LED can irradiate tissue at different wavelengths of light.

In yet another example, the processor 420 can control a bulk temperature or a temperature near an LED of the light source 434 using the heat pump 440. The heat pump 440 can be used to maintain a constant temperature or achieve some desired temperature. Moreover, in some embodiments, the processor 420 can use the heat pump 442 to control a temperature near one or more photodiodes used to detect the light irradiated by an activated LED of the light source 434.

In some embodiments, for example in embodiments directed to implementing high speed spectral sweep analysis discussed in further detail below, the emitter 634 (e.g., LED) temperature, forward voltage and/or current are intentionally changed in order to change the wavelengths of light emitted by the emitters 434. In an embodiment, a temperature, forward voltage and/or current of one or more emitters 434 is intentionally cycled in order to predictably change the wavelength of light emitted by the emitters 434. For example, once the emitters 434 reach an initial known operational state, the temperature, forward voltage, and/or current of an emitter 434 can be intentionally changed to create a different operational state. This process can continue, cycling or sweeping the emitters 434 through different operational states. This process can be repeated during the course of measurement in order to make the emitters 434 irradiate light at different wavelengths and thus enabling collection of information about the sample tissue at different wavelengths. In some embodiments, temperatures are swept between about 15 degrees Celsius and about 45 degrees Celsius. In an embodiment, temperatures are swept between about 20 degrees Celsius and about 40 degrees Celsius. In some embodiments, the temperature of the emitters 434 is varied by altering the forward voltage, the drive current, the duty-cycle of the emitters 434, or a combination of the above. In some embodiments the emitter 434 temperature is swept in an uncontrolled way by allowing the temperature to heat up naturally through the process of driving current through the LED.

By varying emitter 434 temperatures and thereby causing the emitter 634 to sweep through a range of wavelengths, greater absorption information can be determined. For example, the information gained from sweeping the wavelengths can be used to characterize a slope of the absorption curve. This information can be used to obtain more accurate results. Emitter 434 temperature changes can also force emitted wavelengths to a predetermined, known centroid or interpolation point, reducing processing requirements and increasing accuracy. Additionally or alternatively, the act of sweeping emitter 434 temperatures effectively creates additional wavelengths without affecting path length or requiring a large number of emitters 434. These additional wavelengths can be used in the calculation of the physiological parameters. SLED wavelengths can also be deconvolved such that the full wavelength information from the SLED spectrum can be used rather than just a single average point (i.e., the SLED centroid wavelength), which will provide higher spectral resolution data. The deconvolution can be performed by characterizing the full spectral changes of a SLED at the drive current, duty cycle, and temperature that the SLED will be operated at and using this a priori spectral information to extract the full wavelength information during runtime.

Figure 5:
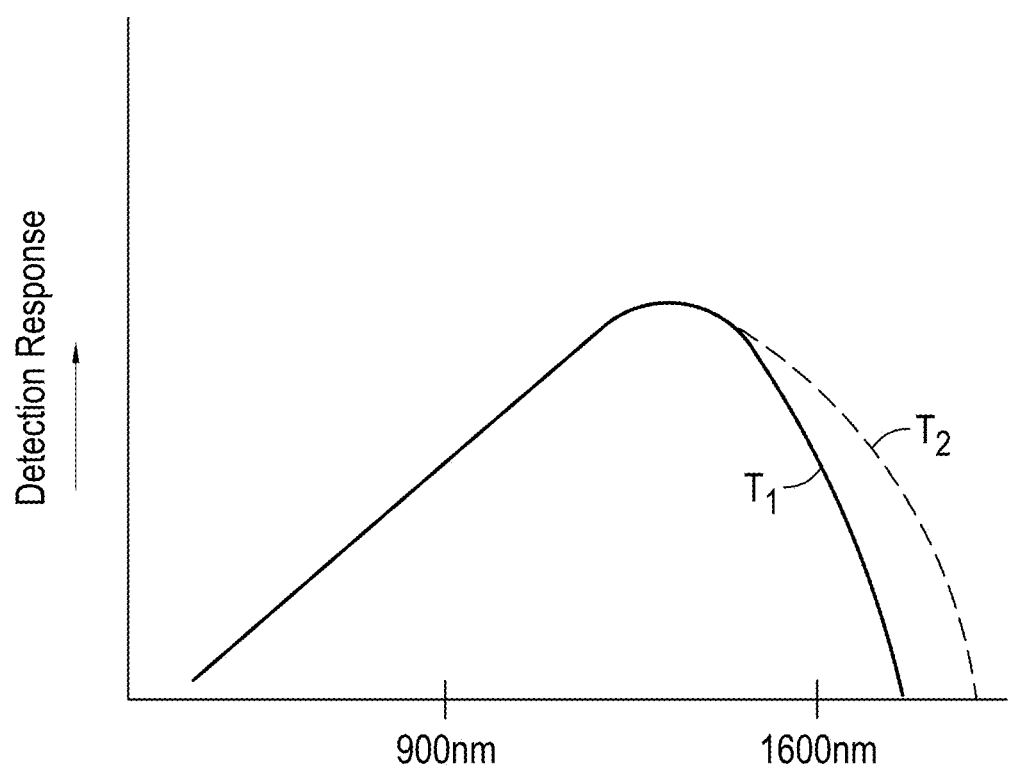
FIG. 5 illustrates an example of a detector response based on wavelengths measured and temperature variations.

FIG. 5 illustrates generally a detection profile of an indium gallium arsenide (InGaAs) photodetector 306 based on wavelength and temperature. For certain wavelengths, for example around about 1500 nm, the detection profile is flat and detector 306 measurements are relatively unaffected by temperature shifts. However, for longer wavelengths beyond about 1520 nm, significant signal degradation can occur with temperature shifts. Thus, controlling the temperature of the detector 306, particularly for certain wavelengths, can stabilize DC measurements to improve accuracy.

Attention is now directed to embodiments of the present disclosure that are configured to perform high speed spectral sweep analysis to non-invasively predict, among other analytes, glucose in tissue. A spectrometer is disclosed that spans (or sweeps) specific wavelength regions and collects intensity data of light through tissue. The measured light intensity through the tissue ($I_T$) is divided by intensity fluctuations from the light source ($I_0$) to derive the sample tissue bulk absorbance ($Abs_T$). The relationship between these parameters can be expressed as:

$$\text{Transmittance} = \frac{I_T}{I_0} = 10^{-Abs_T} \quad (1)$$

$$\text{Bulk Absorbance} = Abs_T = \text{LOG}_{10}\frac{I_0}{I_T} \quad (2)$$

Using empirical clinical data, an inverse model of the collected data at different blood glucose values can be created and used to predict glucose (or other analyte) values based on the measured tissue bulk absorbance ($Abs_T$) and other parameters collected by the high speed data collection system. Some other examples of parameters that can be used in the development of an inverse model include but are not limited to various measured temperatures (LED, tissue, ambient, photodiode, beam splitter, etc.) and absorbance of various reference materials measured real time. Such a model may be referred to as a "predictive calibration model." For illustration purposes, the present disclosure describes embodiments of systems, devices, and methods employing high speed spectral sweep analysis applied to a direct current (DC) measurement of glucose in tissue. However, one skilled in the art will recognize that the systems, devices, and methods disclosed herein can also be applied to alternating current (AC) measurements of glucose in tissue, as well as to other blood constituents.

The disclosed systems, devices and methods for high speed spectral sweep analysis to non-invasively predict, among other things, glucose in tissue rely on careful control of the environment in which the data is collected. Informative spectral data can be obtained during the sweeping of specific wavelength regions of sample tissue. The spectral measurements are sensitive to sources of error, such as for example, fluctuations in power, temperature, and wavelength, among other things. Accordingly, systems, devices and methods disclosed herein are used to monitor, control and/or adjust for, among other things, variations in emitter light source, emitter temperature, tissue temperature, and photodetector temperature to reduce or eliminate distortion in the collected spectral information that is reflective of blood constituents, such as, for example, glucose. Additionally, the disclosed high speed data collection systems, devices and methods are used to collect a larger quantity of spectral information than can be collected using lower speed, averaged data collection approaches. Tissue sample size is also controlled to reduce distortion and to increase the quantity of useful spectral information collected. Similarly, fixed distances between emitter and detector are implemented to secure useful spectral information. Accurate measurement and/or control of emitter temperature, tissue sample temperature, and photodetector temperature are also disclosed herein, again, to help secure the collection of valuable and useful spectral information reflective of blood constituents, such as glucose.

Figure 6:
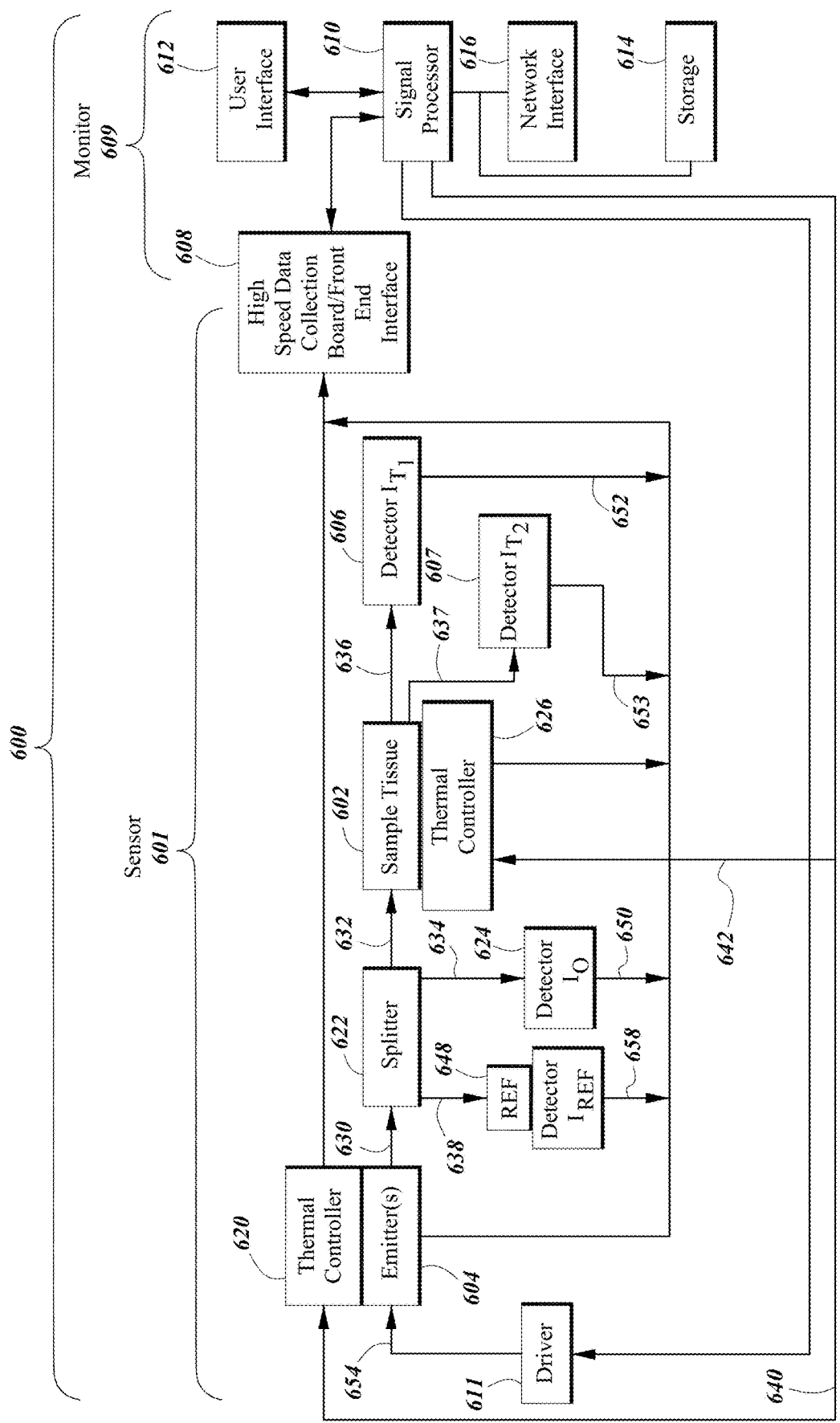
FIG. 6 illustrates a block diagram of an embodiment of a physiological measurement system configured to perform high speed spectral sweep analysis with two different detectors sampling light from two different paths through the tissue.

FIG. 6 is a block diagram illustrating an embodiment of a data collection system 600 that can be configured to perform high speed spectral sweep analysis disclosed herein. In certain embodiments, the data collection system 600 non-invasively measures a blood analyte, such as, by way of non-limiting example, glucose. The data collection system 600 includes a sensor 601 configured to irradiate visible and/or infra-red light to a sample tissue 602 of a patient at a measurement site and then detect the optical radiation that is attenuated by the sample tissue 602. In some embodiments, optical radiation that is reflected by the sample tissue 602 can be detected. The sensor 601 includes one or more emitters 604 that generate the optical radiation, or light source 630. A thermal controller 620, which may also be referred to as a temperature regulation component, can be in thermal contact with the emitter 604 to monitor and/or control the thermal properties of the emitter 604 during operation. The thermal controller 620 can include a temperature sensor, such as for example, a thermistor, to measure the temperature of the emitter 604 during operation. The thermal controller 620 can also include a thermoelectric cooler (TEC), such as for example, a Peltier device, to lower the temperature of the emitter 604. However, one skilled in the art will recognize that the TEC can be electrically reversed to increase the temperature of the emitter. Therefore, through the use of an adequate electrical current, the emitter temperature can be fully and well controlled in a certain or desired range. A heat sink can be thermally coupled to a "hot end" of the TEC to dissipate heat. Thus, the thermal controller 620 serves as a circuitry based temperature alteration device. The thermal controller 620 communicates with a high speed data collection board/front end interface 608 to transmit temperature information of the emitter 604 to the high speed data collection board/front end interface 608. The temperature information can be transmitted to the signal processor 610, and the signal processor 610 can use the emitter 604 temperature information to adjust signal processing parameters to compensate for temperature variations of the emitter 604. According to an embodiment, the signal processor 610 is connected to the thermal controller 620 and therefore can transmit a thermal control signal 640 to the thermal controller 620 to regulate the temperature of the emitter 604 during operation. In some embodiments, regulation and control of the thermal controller 620 is performed by the high speed data collection board/front end interface 608. In other embodiments, the signal processor and/or the high speed data collection board/front end interface 608 can control the thermal controller 620. Regulation of emitter 604 temperature can be used to vary (or sweep) the wavelength of the light source 630 at a desired rate or shape.

Measurement of the emitter light source 630 within the emitter electronics package is performed to account for power changes to the optical radiation emitted by the emitter 604. Methods to obtain accurate measurement of the emitter light source 630 ($I_0$), including fluctuations thereto, are disclosed to help derive a sample tissue bulk absorbance ($Abs_T$) that is useful in predicting, for example, the glucose level of the sampled tissue. The light source 630 emitted from the emitter 604 is directed to a splitter 622. The splitter 622 splits the emitted light source 630 into a plurality of beams. For the purpose of this disclosure, it splits the light into a first beam 632, into a second beam 634 and into a third beam 638. The first beam 632 comprises a portion of the light source 630 that is emitted from the emitter 604 and used to irradiate the sample tissue 602 of the patient. The second beam 634 comprises a fractional portion of the light source 630 that is directed to a detector 624 configured to measure the fractional portion of the light source 630 for use in determining intensity fluctuations from the light source ($I_0$), which in turn, is used to derive the bulk absorbance ($Abs_T$) of the sample tissue 602. The third beam 638 comprises a fractional portion of the light source 630 that is directed to a reference absorption material 648 and to a detector 628 configured to measure the fractional portion of the light source 630 for use in determining spectral content of light source (Iref), which in turn, is used to derive the bulk absorbance ($Abs_T$) of the sample tissue 602. The reference absorption material 648 shall have a known absorption profile. The ideal reference absorption material 648 shall be stable over time such that it does not shift with wavelength or with absorption. One example of a reference absorption material is water sealed in a cuvette. The advantage of water is that it has a similar absorption profile to the tissue sample site which gives it an advantage to be able to capture real-time wavelength changes. Another example of a reference absorption material 648 is didymium oxide glass. Other materials, including other rare earth oxide glass materials may be used as the reference absorption material 648. The reference absorption material 648 may also comprise a plastic such as polystyrene, polycarbonate, or an acrylic.

In some embodiments, the emitter light source detector 624 is optically coupled to the emitter 604 to help prevent dissipation of, or interference from other light sources with, the second beam 634. In an embodiment, optical grade polytetrafluoroethylene (PTFE), also known by the brand name Teflon™, is used to mix, attenuate, and optically couple the emitter light source detector 624 to the emitter 604. Optical grade PTFE possesses optical properties that remain constant over a wide range of wavelengths, spanning from the ultraviolet to the near infrared wavelengths. When transmitting optical radiation in this range of wavelengths, the relation of PTFE's regular transmittance to diffuse transmittance is negligible, thereby serving as an optical coupler that can transmit optical radiation with minimal loss, distortion, or interference. Thus, optical grade PTFE is a suitable material to couple the fractional portion of the light source 630 from the emitter 604 to the emitter light source detector 624, which may be optically shielded to prevent losses or distortion.

In an embodiment the emitter light source detector 624, such as a photodiode, is optically coupled to the emitter 604 to measure the light generated by the emitter 604. The emitter light source photodetector 624 is configured to sample a predetermined fraction of the light that will enter the sample tissue. The fractional portion of the emitted light that is measured by the emitter light source photodetector 624 is a complete, scaled representation of the light delivered to the sample tissue 602, having a power and wavelength distribution, such that the ratio of $I_T/I_0$ should not change with fluctuations in light source power due to temperature, drive current, duty cycle, or the like. The emitter light source photodetector 628 is configured to sample a predetermined fraction of the irradiated light that is directed to a reference spectral sample 648. The fractional portion of the light that is measured by the photodetector 628 is an attenuated portion of the light delivered to the sample tissue 602, having power and wavelength distribution attenuated by the reference sample 648 such that the ratio of $I_{REF}/I_0$ should take into account the spectral information caused by the intentional changes in source temperature, drive current, duty cycle, or the like. In another embodiment there can be more than one reference sample 648 and photodetector reference channels 628. A specific example would be one reference sample that is a pure water filled cuvette and another reference sample that is a cuvette filled with water and a predetermined concentration of glucose.

Accordingly, the measured emitter light source ($I_0$) 650 and the measured light intensity transmitted through the tissue ($I_T$) 652 and 653 should change in the same proportion as do the power or wavelength fluctuations of the emitted optical radiation 630. Similarly, the emitted light source (Iref) 658 should also change based on the spectral response of the filter 648. In an embodiment, the first beam 632 comprises ninety-nine percent of the emitted light source 630, and the second beam 634 and the third beam 638 comprise one percent of the emitted light source 630. Of course, a skilled artisan will appreciate that other percentages may be used without departing from the teaching of the present disclosure.

The sample tissue 602 may also be in thermal communication with a thermal controller 626 to monitor and/or regulate the temperature of the sample tissue 602 during measurement. As described above, the thermal controller can comprise a temperature sensor, a TEC, and a heat sink. As illustrated in FIG. 6, the thermal controller 626 is connected to the high speed data collection board/front end interface 608 which is configured to receive signals from the various components of the sensor 601, process (or preprocess) the signals, and transmit the processed (or preprocessed) signals to the signal processor 610. The signal processor 610 can use sample tissue 602 temperature information to adjust signal processing parameters to compensate for temperature variations in the sample tissue 602. In some embodiments, the signal processor 610 is connected to the thermal controller 626 and therefore can transmit a thermal control signal 642 to the thermal controller 626 to regulate the temperature of the sample tissue 602 during operation. In other embodiments, control of the thermal controller is performed by the high speed data collection board/front end interface 608. In other embodiments, the signal processor and/or the high speed data collection board/front end interface 608 can control the thermal controller 626. In another embodiment the reference sample 648 can have an independent thermal controller (not shown) to control the reference sample to a fixed temperature or to match the temperature of the sample tissue 602. The sensor can also be designed in a way to couple the reference material and the sample tissue such that they have the same or similar temperatures.

The first beam 632, directed at the sample tissue 602, is attenuated by the sample tissue 602. The attenuated light 636 and 637 are detected by multiple tissue light detectors 606 and 607 which measure the light intensity through the tissue ($I_{T1}$ and $I_{T2}$), corresponding to the attenuated light 636 and 637. In some embodiments, the tissue light detectors 606 and 607 are placed at different locations in order to create different tissue paths that the light 636 and 637 pass through. In some embodiments, the tissue light detector 606 or 607 measures light that is reflected from the sample tissue 602. The tissue light detectors 606 and 607 are connected to the high speed data collection board/front end interface 608 which is configured to receive signals from the various components of the sensor 601, process (or pre-process) the signals, and transmit the processed (or pre-processed) signals to the signal processor 610.

The high speed data collection board/front end interface 608 is configured to support high speed spectral sweep analysis for non-invasive measurement and prediction of blood constituents, such as, for example, glucose. According to an implementation, a fully differential path is implemented using, for example, a transimpedance amplifier to reduce near field crosstalk and to provide immunity from noise. The high speed data collection board/front-end interface 608 is simplified (as compared to other embodiments previously described) by removing certain stages included in other embodiments of the front end interface. For example, a programmable gain amplifier (PGA) stage can be eliminated, a high pass filter stage can be eliminated, and a single-ended to differential-ended stage can be eliminated. A field programmable gate array (or similar type of device) can be used to implement a multi-stream, high-throughput serial bus to support the high speed data collection to implement the methods of high speed spectral sweep analysis disclosed herein. Moreover, high accuracy, successive approximation register ADCs can be used (as opposed to other types of ADCs) to reduce or to substantially eliminate ringing effects during spectral sweeping. A person skilled in the art may recognize that the herein described ringing is frequently observed on data processed by digital filters such as, for example, a FIR filter.

The data collection system 600 also includes a monitor 609 comprising the signal processor 610, a user interface connected to the signal processor, a storage device 614 and a network interface device 616, which are connected to the signal processor 610. As shown in FIG. 6, the monitor 609 can include the signal processor 610 and a user interface, such as a display 612. The monitor 609 can also include optional outputs alone or in combination with the display 612, such as a storage device 614 and a network interface 616. In an embodiment, the signal processor 610 includes processing logic that determines measurements for desired analytes, such as glucose, based on the signals received from the detectors 606, 624. The signal processor 610 can be implemented using one or more microprocessors or subprocessors (e.g., cores), digital signal processors, application specific integrated circuits (ASICs), field programmable gate arrays (FPGAs), combinations of the same, and the like.

Wavelength sweeping can be performed, among other methods, by controlling and/or changing the temperature of the emitter 604, by controlling and/or changing the current delivered to the emitter 604, by controlling and/or changing the duty cycle of the signal that drives the emitter 604, and in some instances, by allowing the temperature of the emitter 604 to fluctuate freely. Some embodiments of the disclosed high speed spectral sweep analysis systems, devices, and methods include the use of at least one emitter 604 capable of emitting wavelengths that are useful in detecting blood constituents, such as, for example, glucose. The emitter 604 serves as the source of optical radiation transmitted toward the measurement site. The emitter 604 can include one or more sources of optical radiation, such as light-emitting diodes ("LEDs") including, by way of non-limiting example, top-emitting LEDs, side-emitting LEDs, superluminescent LEDs ("SLEDs"), laser diodes, incandescent bulbs with appropriate frequency-selective filters, combinations of the same, or the like. In an embodiment, the emitter 604 includes sets of optical sources 604 that are capable of emitting visible and near-infrared optical radiation. Each emitter 604 is manufactured to emit optical radiation at a specific centroid wavelength, within certain tolerances. However, in practical implementation the wavelength emitted by an emitter 604 can fluctuate based on, for example, variations in the temperature of the emitter 604, the amount of current supplied to the emitter 604, and the duty cycle (i.e., the percentage of time within a period that a signal is active) of the signal that drives the emitter 604. By controlling these parameters, among others, the systems, devices and methods disclosed herein can cause the emitter 604 to sweep through a range of wavelengths to support collection of valuable spectral information.

Wavelength sweeping can be implemented by controlling the temperature of the emitter(s) 604 to intentionally vary the wavelength of optical radiation 630 emitted from the emitter(s) 604. In an embodiment, the thermal controller 620 comprising a thermoelectric cooler can be used to help perform such temperature control. The principle of thermoelectric cooling, based on the Peltier effect (also known generally as the thermoelectric effect), creates heat flux at a junction between two different types of materials. A Peltier device, which may function as a cooler, a heater, or a thermoelectric heat pump, is a solid state device configured to transfer thermal energy from one side of the device to the other side of the device, with the consumption of electrical energy, depending on the direction of the applied current. A Peltier device may also be referred to as a Peltier heat pump, a solid state refrigerator, or a thermoelectric cooler (TEC). A Peltier device can be used for heating, cooling or as a temperature controller that both heats and cools. However, the most commonly used application of Peltier devices is for cooling. Advantages of Peltier devices include the ability to control temperatures to within fractions of a degree, controllability by varying input voltage or current, lack of moving parts, lack of circulating liquid (e.g., a refrigerant), long life, high reliability, flexible shape and form factors, and small size. In operation as a thermoelectric cooler a voltage is applied across the device which leads to a difference in temperature between the two sides of the TEC. As DC current flows through the device, heat is transferred from one side of the device to the other. Thus one side becomes cooler while the other side becomes hotter. The hotter side of the device can be attached to a heat sink to dissipate some of the generated heat and maintain the "hot side" of the device at a desired temperature, such as, for example, ambient temperature. The cooler side of the device can be maintained below ambient temperature.

Variation of the drive current 654 delivered to an emitter 604 can also cause the emitter 604 to sweep through a range of wavelengths. The signal processor 610 can control the current controller, or driver 611, to vary the current delivered to the emitter 604 in a manner such that the emitter 604 sweeps through a desired range of wavelengths, by way of non-limiting example, by changing the current in a linear fashion or other types of waveforms. In some embodiments the signal processor 610 can vary the duty cycle of the signal 654 that drives the emitter 604 in a manner to cause the light source 604 to sweep through a desired range of wavelengths. In some embodiments the emitter 604 is a SLED. The emitter 604 may also be allowed to sweep through a range of wavelengths based on the naturally-occurring changes in temperature of the emitter 604. Additionally, control of the emitter's 604 natural heating and cooling times can be modified by changing heat sinking properties of the electronics package in which the emitter 604 is implemented.

In an embodiment configured to predict glucose levels, a wavelength range from approximately 1300 nm to approximately 1650 nm is used. This wavelength range can be spanned, or swept, by selecting a number of distinct wavelengths to separate glucose from water. In an embodiment, three distinct wavelengths are selected, and in an embodiment four distinct wavelengths are selected. One skilled in the art will appreciate that different numbers of distinct wavelengths may be used without departing from the teaching of the present disclosure. In an embodiment, the distinct wavelengths can be used to measure and correct for fluctuations of temperature in the sample tissue 602 being measured. In an embodiment configured to predict glucose levels, a wavelength range of approximately 1330 nm to approximately 1400 nm may be used. This wavelength range can be spanned by a single emitter 604, such as, for example, a super-luminescent LED. Additionally, this wavelength range can be used to correct for scattering and temperature fluctuations in the tissue being measured. In an embodiment, a wavelength range of approximately 500 nm to approximately 1750 nm may be used to measure constituents of blood, such as, by way of non-limiting example, various hemoglobin constituents, cholesterol, lipids, and the like.

Systems, devices and methods directed at collecting data at high speeds (as compared to relatively lower speed, averaged data collection methods frequently used in pulse oximetry systems) are used to capture spectral information that is useful in predicting, for example, glucose levels in tissue. Emitters 604 are typically modulated at a duty cycle of approximately ten percent, though it is understood that various other duty cycles can be used. During the time that the emitter 604 is active (i.e., emitting light), the junction temperature of the emitter 604 increases. The temperature increase causes a power drop and a red shift of wavelength, which may be referred to as a "high speed crown." A spectral sweep occurs during the high speed crown which provides valuable spectral information that is useful in determining constituents in tissue, such as for example, glucose. A skilled artisan will appreciate that "red shift" means an increase in the wavelength, while a "blue shift" means a decrease in the wavelength of emitted light.

Figure 7:
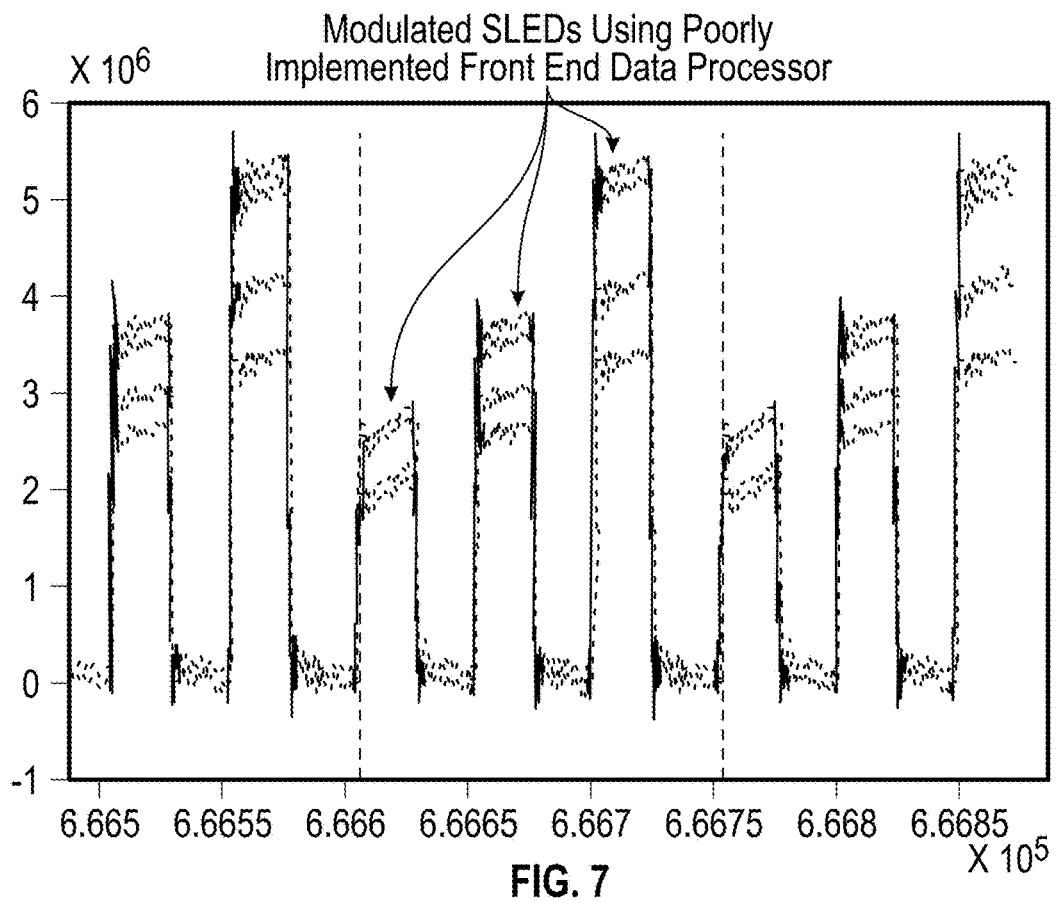
FIG. 7 illustrates a signal processed by a low fidelity data collection board in which emitters are modulated to sweep through a range of wavelengths.

A challenge in the signal processing of high speed crowns is that noise in the form of ringing can be present. Such ringing-based noise can prevent successful extraction of the valuable spectral information contained in the high speed crown. The ringing is an inherent property of certain analog-to-digital converters (ADCs) commonly used in processing the collected high speed crown data, such as, for example, sigma-delta ADCs and oversampling type ADCs, to name a few. FIG. 7 illustrates examples of noise caused by ringing. As shown, the effect of ringing distorts the spectral information that is useful in determining constituents in blood.

Figure 8:
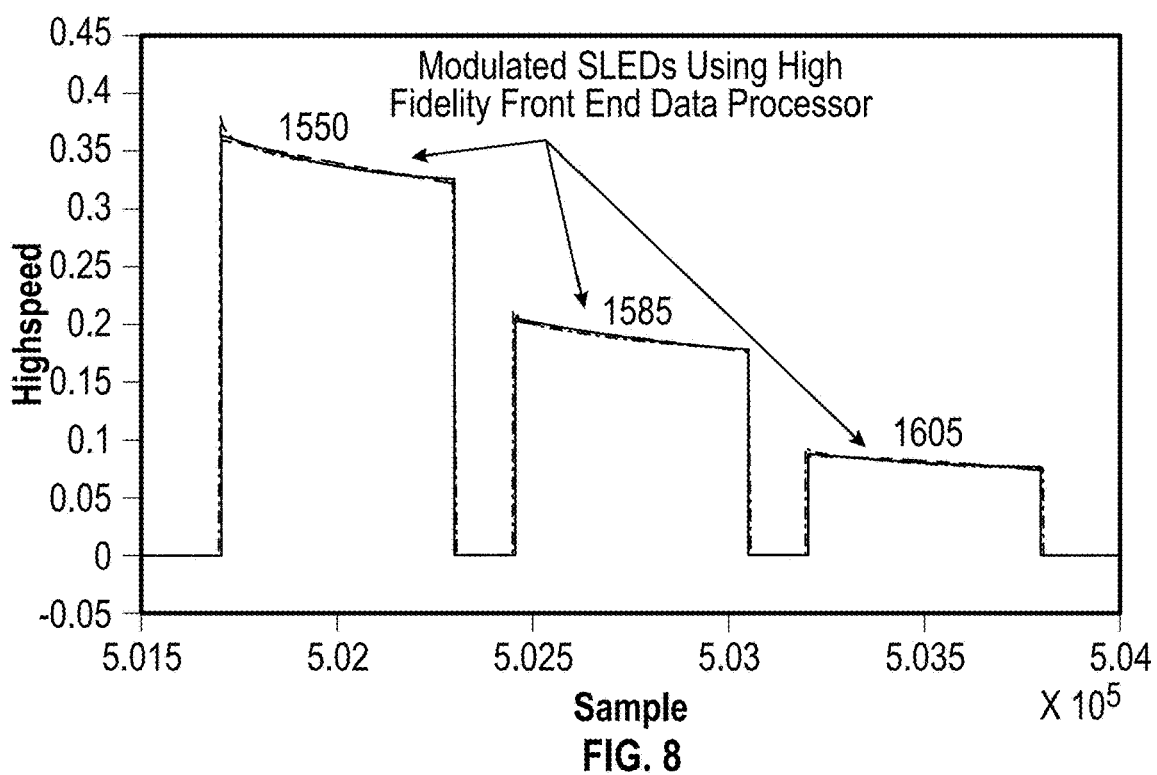
FIG. 8 illustrates a signal processed by a high fidelity, high speed data collection board in which emitters are modulated to sweep through a range of wavelengths.

It is possible to substantially reduce or effectively eliminate this ringing phenomenon by using high-accuracy, successive approximation register (SAR) ADCs to acquire raw high speed crown data. FIG. 8 illustrates examples of high speed crowns acquired by a high accuracy SAR ADC. As shown, the signals processed using a high-accuracy SAR ADC eliminate the distortion caused by ringing, thereby making it possible to obtain the valuable spectral information in the high speed crowns for use in determining constituents in blood, such as glucose. High speed crowns of a given LED can be used to calculate a tissue absorption segment over the spectral sweep that occurs in the crown by using equation 2 above. The tissue absorption segments can be combined from different crowns into tissue absorption bands. An example of tissue absorption bands for three SLEDs is provided in FIG. 9. Further deconvolution of multiple LED spectra can be performed in order to capture a full wavelength, high resolution tissue absorption profile by using a priori information of an LED's full spectrum characterized at different currents, duty cycles and temperatures.

In the present disclosure, the size of the sample tissue 602 is also controlled to reduce distortion and to increase the quantity of useful spectral information collected. Similarly, a fixed distance between emitter 604 and detector 606 is implemented to secure useful spectral information. According to certain embodiments for measuring glucose, the sample tissue 602 contains interstitial fluid which can have varying amounts of glucose to be measured.

Interstitial fluid comprises a thin layer of fluid that surrounds the cells of a body. In humans, interstitial fluid makes up approximately forty percent of the water in the body and thus accounts for approximately one-sixth of a human's body weight. Interstitial fluid serves as a source of fuel for cells, comprising glucose, salt, fatty acids, and minerals including calcium, magnesium, and potassium. Blood capillaries provide the nutrients to the interstitial fluid. Accordingly, levels of a blood constituent, such as glucose, in interstitial fluid can reflect (with an acceptable degree of accuracy) levels of that constituent in blood. In certain embodiments of the present disclosure, skin is used as the sample tissue 602 on which measurements are taken.

To reduce variability of measurements, thickness of the sample tissue 602 is controlled in a manner such that the distance between the emitter 604 and the detectors 606 and 607 is fixed. In some embodiments, the thickness of the sample tissue 602 can be controlled to have different distances between the emitter 604 and the different detectors 606 and 607. In some embodiments, in order to have the sample tissue 602 fit within the fixed distance between the emitter 604 and the detectors 606 and 607 without stretching or deforming the tissue in an undesirable way an application of a coupling agent, such as, by way of non-limiting example, a perfluorinated liquid. In some embodiments, the webbing between a subject's thumb and index finger is used as the sample tissue 602. In some embodiments, a skin-fold pinch, which may be collected anywhere on the patient's body, comprises the sample tissue 602. A skilled artisan will appreciate that many other portions of a subject's body may serve as sources of sample tissue 602 without departing from the teachings of the present disclosure. A skilled artisan will also appreciate that many more detectors placed at different locations can be used without departing from the teachings of the present disclosure.

Referring again to FIG. 6, in some embodiments, the temperature of the sample tissue 602 is controlled and/or compensated for during non-invasive measurement. Water absorption of optical radiation increases significantly at a wavelength of 1450 nm. However, as the temperature of water increases, the absorption wavelength decreases (i.e., blue shifts). As discussed above, to predict glucose levels, a wavelength range from approximately 1300 nm to approximately 1650 nm may be used. Thus, the absorbance of interstitial fluid (comprising mostly of water) in the sample tissue 602 drops as its temperature increases. To compensate for variability in tissue temperature a thermometer (or other temperature sensor known in the art) may be used to determine the sample tissue 602 temperature during measurement by the sensor 601. In an embodiment the temperature sensor is included in the thermal controller 626. Additionally, temperature modeling may be used to determine average sample tissue 602 temperatures or a distribution of sample tissue temperatures through the sample tissue volume. The temperature information can be used to adjust for changes in absorbance of the interstitial fluid to help determine a more accurate measurement of the sample tissue 602 bulk absorbance. In other embodiments, the thermal controller 626 which may comprise passive or active temperature control structures, may be used to control the sample tissue 602 temperature. For example, a TEC coupled to a heat sink can be used to regulate the temperature of the sample tissue 602. In some instances, the sample tissue 602 temperate can be regulated to within 1 degree Celsius. In some embodiments, a temperature sensor is configured to measure the sample tissue 602 temperature during sensor 601 operation. The predictive calibration model can be based on variable tissue temperature (as measured by the sample tissue 602 temperature sensor) to compensate for water absorbance changes due to temperature fluctuations.

Changes in temperature of detectors 606, 607, 624, 628 (e.g., photodiodes) can degrade the integrity of signals used to measure blood constituents. The present disclosure provides systems, devices and methods for controlling and/or compensating for fluctuations of temperature of detectors 606, 607, 624, 628 employed during non-invasive sample tissue measurements. In some embodiments, thermistors (or other temperature sensors) can be coupled to the photodetectors 606, 607, 624, 628 to monitor and/or correct for photodiode temperature variation. In some embodiments, a thermal controller 620, 626, comprising a temperature sensor, a thermoelectric cooler, and a heat sink, may be used to regulate photodiode 606, 607, 624, 628 temperature(s) to within one-tenth or less of a degree Celsius.

In an embodiment, a TEC (not shown) is provided to control the temperature of the photodetectors 606, 607, 624, 628. In an embodiment, an integrating sphere having port holes through which emitted light 630 can be transmitted can be used as the beam splitter. The integrating sphere can be coated with a diffuse material such as Spectralon, optical PTFE or diffuse gold to improve the mixing of the light. Other diffuse coatings that have a flat spectral response can be used as well. The emitted light 630 is directed through a first portal into the integrating sphere. The integrating sphere acting as the beam splitter splits the emitted light 630, allowing a fraction of the emitted light 634 to transmit into an optical coupler that is coupled directly to the emitter light source photodetector 624. The emitter light source photodetector 624 is optically shielded to avoid dissipation of, and interference with, the fractional portion of the emitted light 634 that is directed to the photodetector 624. The emitter light source photodetector 624 is also thermally shielded to minimize susceptibility to thermal fluctuations which might affect the accuracy of the photodetector's 624 measurements. Similarly, a fraction of the emitted light is directed to the detector 628 which is coupled to a reference absorption material 648. The remainder of the emitted light 632 is directed to the sample tissue 602 through a second portal of the integrating sphere 660. In an embodiment, the beam splitter 622 passes 99% of the emitted light 630 to the sample tissue 602, and it passes 1% of the emitted light 630 to the emitter light source photodetectors 624, 628. A skilled artisan will understand and appreciate that other proportions of the emitted light can be split between the emitted light source photodetectors 624, 628 and the sample tissue 602.

Figure 14:
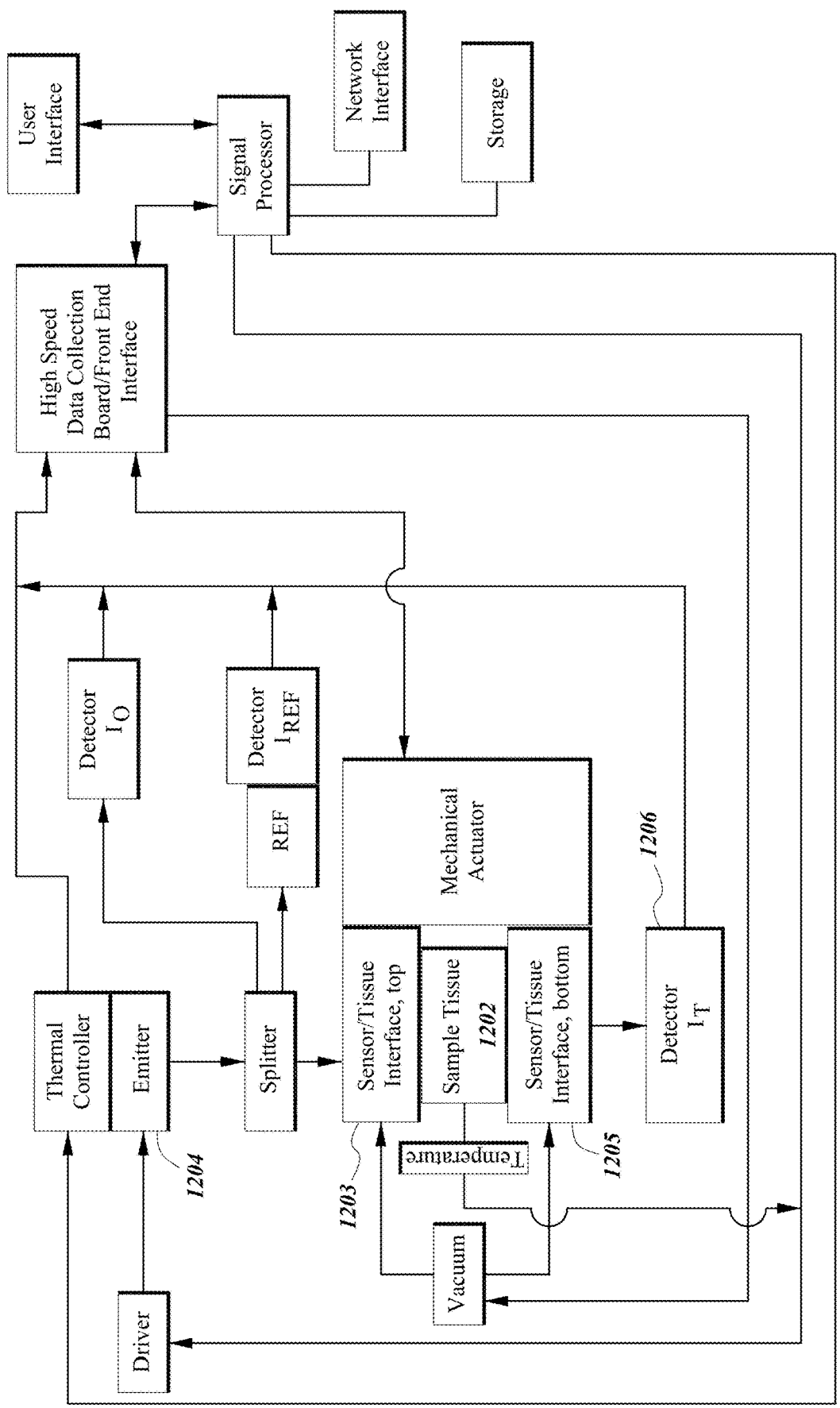
FIG. 14 illustrates a block diagram of an embodiment of a physiological measurement system configured to perform high speed spectral sweep analysis with a mechanical actuator that can adjust and control the sample tissue volume.

In an embodiment, rather than controlling the thickness of the sample tissue 602 the absorbance of the Sample Tissue 1402 can be controlled. FIG. 14 illustrates a possible way to control absorbance of the Sample Tissue 1402. Using an actuator to control the distance between the Emitter 1404 and the tissue Detector 1206 the Sample Tissue 1402 thickness can be adjusted. As the actuator closes the absorbance of the Sample Tissue 1402 will decrease. In order to make the Sample Tissue thickness increase negative pressure can be applied to both sides of the Sample Tissue such that the interface at both sides is pulled into a tissue receptacle 1403 and 1405. As the actuator opens the Sample Tissue thickness will increase and pull water into the tissue volume and therefore the absorbance will increase. By using the actuator with the vacuum the system can adjust to hold the water volume (or absorbance) in the Sample Tissue constant over time and from measurement to measurement. This can allow for improved placement repeatability and a more controlled data set when generating a calibration curve. The actuator control can also be used to change the thickness of the tissue in a controlled way in order to collect optical data at multiple Sample Tissue thicknesses.

Figure 9:
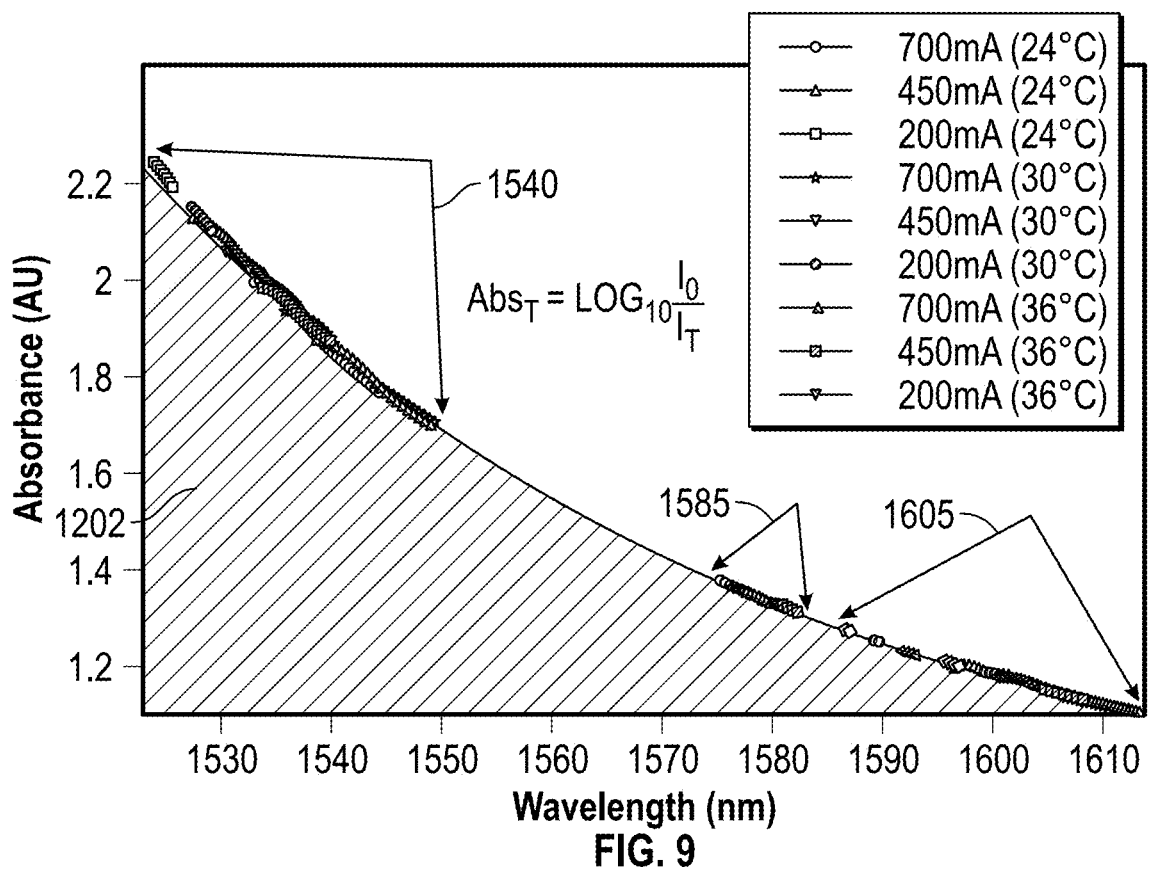
FIG. 9 illustrates results from an implementation of the disclosed high speed spectral sweep analysis system.

FIG. 9 illustrates results from an implementation of the disclosed high speed spectral sweep analysis system which was implemented to measure sample solutions (representing sample tissue 602) of having varying concentrations of glucose in water. A thermal controller 620, controlled by the high speed data collection board 606, was thermally coupled to SLED emitters 604 to vary the temperature of the SLED emitters 604 during operation. A second thermal controller 626, controlled by the high speed data collection board 606, was thermally coupled to the sample solution (representing sample tissue 602) to maintain the sample solution's to a known temperature e.g., at 24° C. A temperature sensor was connected to the photodetector 606 measuring light attenuated by the sample solution to monitor temperature fluctuations of the detector 606. Control of the temperature of the photodetectors 606, 624 was performed by placing the entire sensor 601 including the photodetectors 606, 624 in an environmental chamber (not shown) configured to maintain a controlled ambient temperature of e.g. 24° C. The measured light intensity through the tissue ($I_T$) was measured by the photodetector 606, while the light intensity from the SLED emitters 604 ($I_O$) was measured by the photodetector 624. The distance between the emitter 604 and the detector 606 was known and fixed. The sample solutions were randomized to have differing concentrations of glucose ranging from 0 to 600 mg/dL each day, and the system operated for four consecutive days (after three days used for training). Based on the provided measurements, the signal processor 606 determined the bulk absorbance ($Abs_T$) of the sample solution.

As illustrated in FIG. 9, the three SLED emitters 604 discontinuously spanned a wavelength range between 1520 nm and 1615 nm. By varying driver current to, and temperature of, the SLED emitters, the emitted wavelengths were varied, thereby providing a sweep of wavelengths to provide spectral information to be analyzed by the disclosed system. In particular, a first emitter 604 configured to emit light at a wavelength of 1540 nm swept an approximate range of wavelengths between 1520 nm and 1550 nm. A second emitter 604 configured to emit light at a wavelength of 1585 nm swept an approximate range of wavelengths between 1576 nm and 1582 nm. A third emitter 604 configured to emit light at a wavelength of 1605 nm swept an approximate range of wavelengths between 1588 nm and 1615 nm. The sweeps were implemented by adjusting the drive current for each emitter to three discrete levels (700 mA, 450 mA, and 200 mA), and by adjusting the temperature of each emitter 604 to three discrete temperatures (24° C., 30° C., and 36° C.), yielding nine separate emitted wavelengths for each of the three emitters, comprising a total of twenty-seven measurements. The values plotted in FIG. 9 reflect the derived bulk absorbance ($Abs_T$) for each of the twenty-seven measurements. Below the plotted values is a curve 1202 representing the absolute water spectrum obtained by use of a benchtop spectrophotometer system, generated for purposes of comparison. The plotted values, generated by the disclosed high speed spectral sweep analysis correlate with the curve 1202, demonstrating validity of the disclosed high speed spectral sweep analysis systems, devices and methods for determining bulk absorbance of a sample tissue.

As previously described with respect to FIG. 8, signals processed using a high-accuracy SAR ADC eliminate the distortion caused by ringing, thereby making it possible to obtain the valuable spectral information in the high speed crowns for use in determining constituents in blood, such as glucose. High speed crowns of a given LED can be used to calculate a tissue absorption segment over the spectral sweep that occurs in the crown by using equation 2 above. The tissue absorption segments can be combined from different crowns into tissue absorption bands. An example of tissue absorption bands for three SLEDs is provided in FIG. 9. Further deconvolution of multiple LED spectra can be performed in order to capture a full wavelength, high resolution tissue absorption profile by using a priori information of an LED's full spectrum characterized at different currents, duty cycles and temperatures.

Figure 10A:
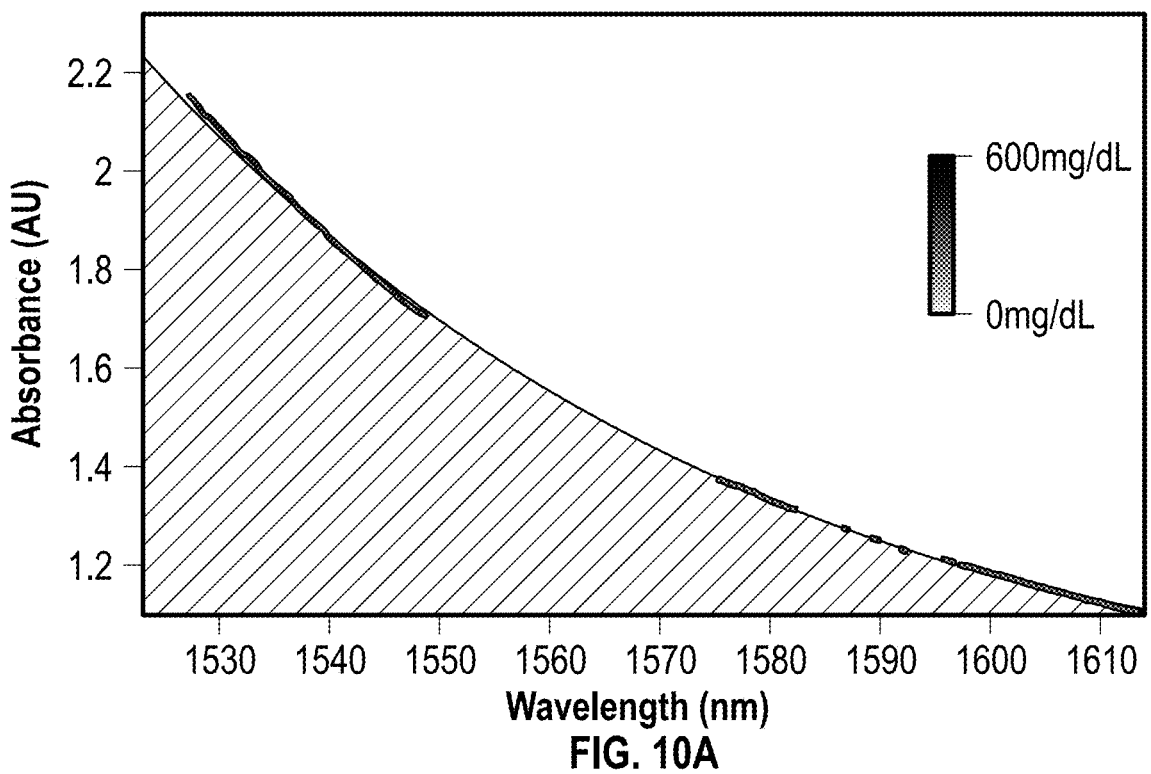
FIGS. 10A-D illustrate zoomed-in results from an implementation of the disclosed high speed spectral sweep analysis system.
Figure 10B:
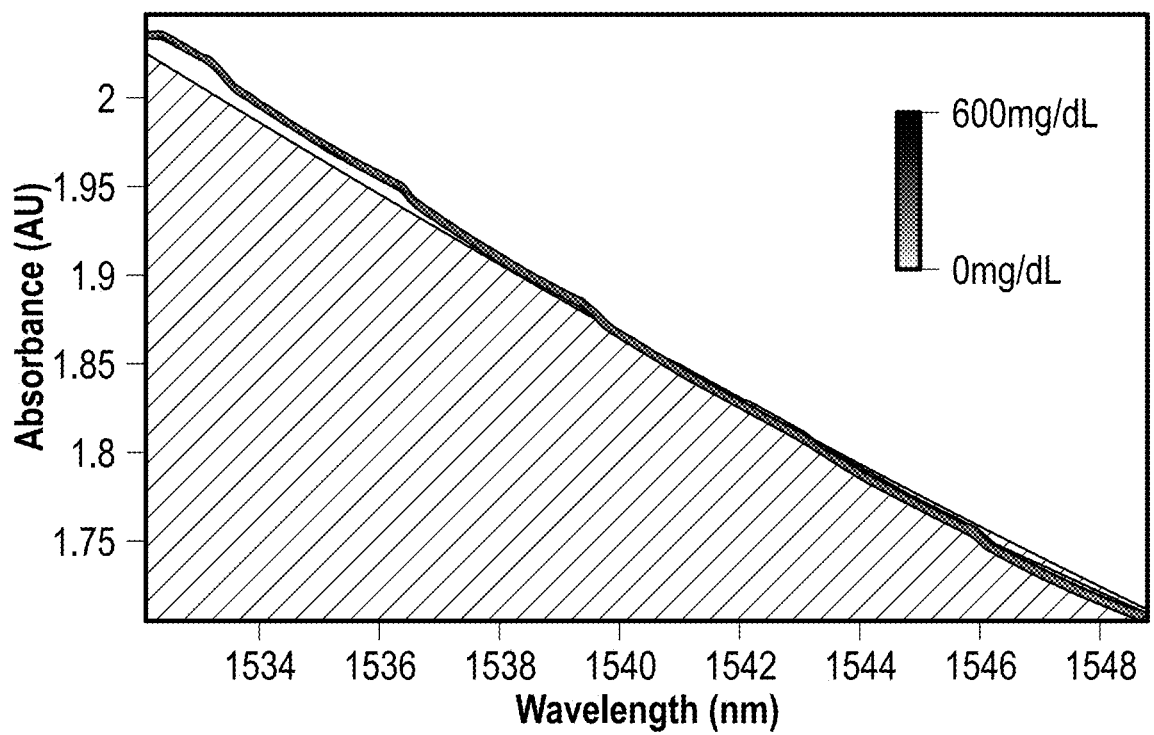
Figure 10C:
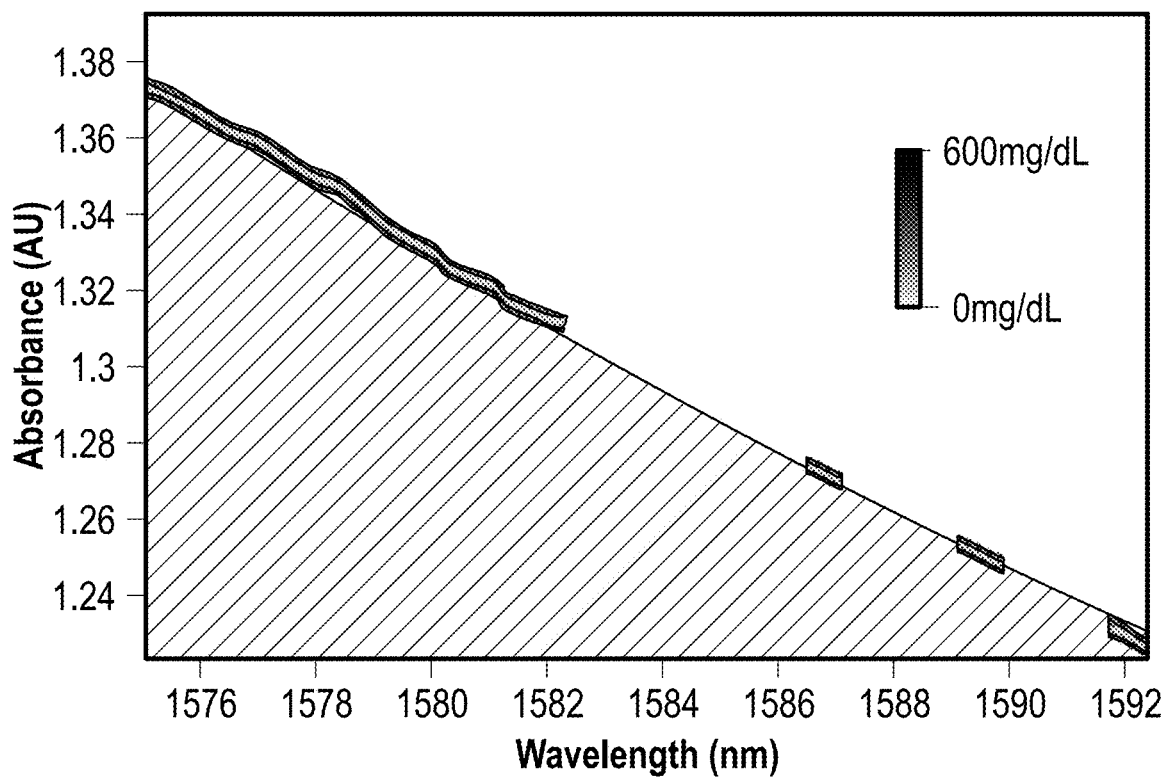
Figure 10D:
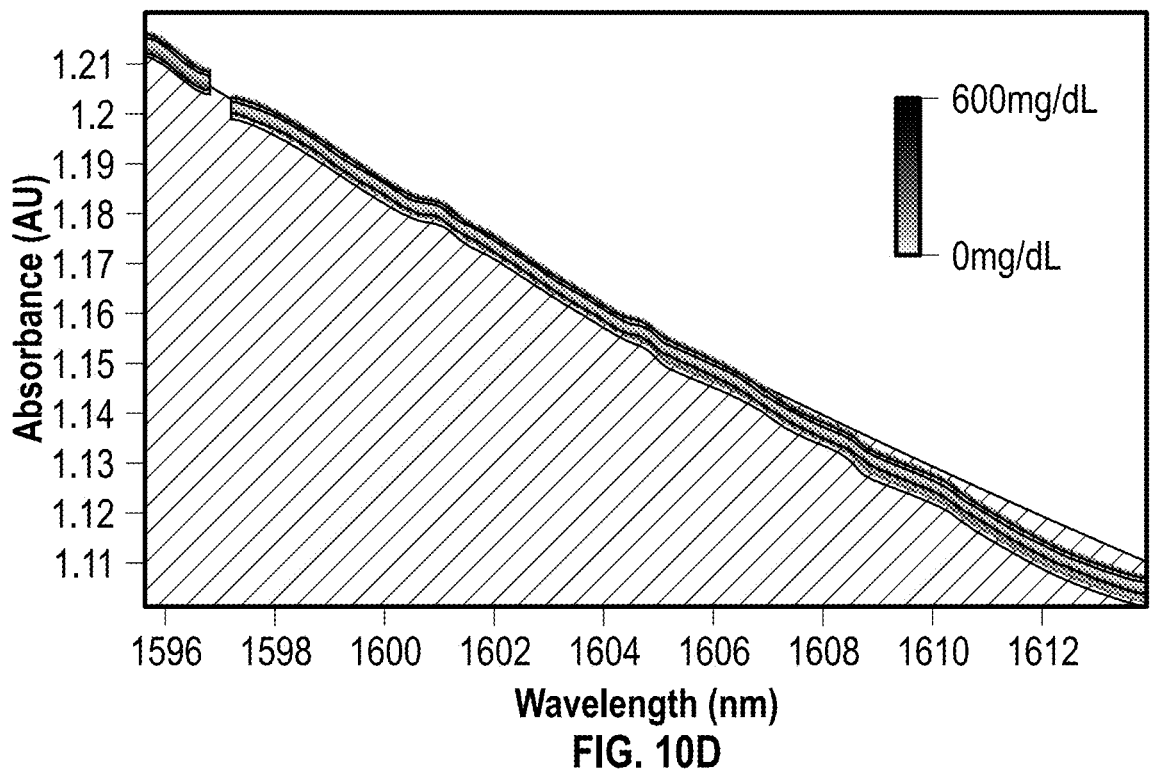

FIG. 10A illustrates the averaged wavelengths of overlapped data (i.e., data collected on multiple days having differing concentrations of glucose ranging from 0 to 600 mg/dL) corresponding to the discontinuously swept wavelength ranges between 1520 nm and 1615 nm of FIG. 9. In particular, the overlapped data reflects measurements of the different sample solutions (representing sample tissue 602) having varying concentrations of glucose. The graphed data of FIG. 10A exhibit sensitivity to glucose as the detected concentrations of glucose correspond to the various concentrations of glucose of the sample solutions. FIGS. 10B-D present enlarged portions of the data presented in FIG. 10A. In particular, FIG. 10B illustrates an enlarged portion of the graph depicted in FIG. 10A, centered around the wavelength of 1540 nm; FIG. 10C illustrates an enlarged portion of the graph depicted in FIG. 10A, centered around the wavelength of 1585 nm; and FIG. 10C illustrates an enlarged portion of the graph depicted in FIG. 10A, centered around the wavelength of 1605 nm. As can be seen more clearly in the enlarged portions depicted in FIGS. 10B-D, the plotted lines illustrate sensitivity to glucose. FIG. 11 illustrates correlation between the reference concentration of glucose in solution (on the x-axis) and the predicted concentration as determined by the disclosed high speed spectral sweep analysis systems, devices and methods (on the y-axis). The average root mean square deviation is 14 mg/dL, corresponding to acceptable measurement accuracy levels for analytes like glucose.

Figure 13:
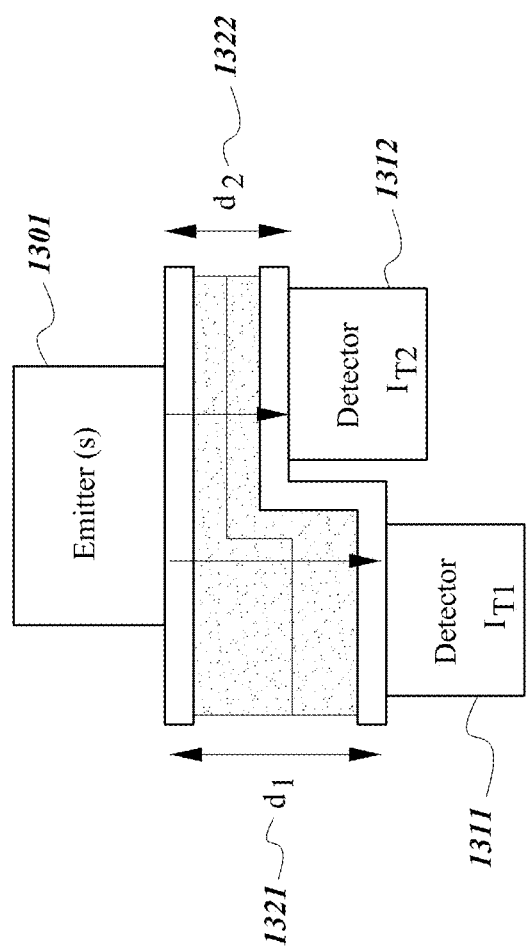
FIG. 13 illustrates a cross-sectional view of the embodiment described in FIG. 12.

FIG. 13 is a cross-sectional view of an embodiment described in FIG. 12 where the two photodiode channels are oriented transverse to the sensor head and are placed on sample tissue opposite the emitter(s) 1301 and at two distinct distances $d_1$ 1321 and $d_2$ 1322. The detectors 1311 and 1312 receive signals $I_{T1}$ and $I_{T2}$ respectively. The tissue sample can be separated into multiple compartments. A simple compartment model includes a layer of epidermis on top and bottom at the outermost surfaces which are in contact with the emitter(s) 1301 and detectors 1311 and 1312. For the shorter distance $d_2$ the tissue can be compressed such that the two layers of skin are in contact and the epidermis and dermis are compressed such that just a small amount of extra cellular fluid occupies the optical path. For the larger distance $d_1$ the tissue spacing allows interstitial fluid, the extra cellular fluid to fill the gap within the optical path. The two different signals measured on the tissue $I_{T1}$ and $I_{T2}$ allow for both data streams to be processed in fitting for glucose. Within the tissue the glucose resides predominantly in the interstitial fluid, so the signal $I_{T1}$ will contain the predominant glucose signal in contrast $I_{T2}$ will have a minimal glucose signal since the interstitial fluid has all been pushed out due to compression of the tissue. Such detector geometry can be used for measurement of glucose as well as tissue hydration and other tissue constituents. Given the difference in pathlengths the following equations can be used to formalize the measured signal. As with pulse oximetry the difference in the two pathlengths can be used to describe an AC signal and a DC signal and ratios of the various signals can be taken to calibrate out any effect of the instrument response of the system.

Another embodiment of a differential pathlength sensor could be to use a system with a minimum of one photodiode such as the sensor depicted in FIG. 2. As described previously the sensor includes a depth stop 208 which serves to define a fixed distance between the emitter shell 204 and the detector shell 206, thereby defining a known path length between emitter(s) and detector(s). The sensor could be designed such that the depth stop is mechanically adjustable to multiple known distances such that using the same emitter(s) and detector(s) paired one can take measurements while actively changing the path length of the tissue between the emitter(s) and detector(s). One advantage to this embodiment would be that the same detector(s) would be used for all the data acquired, which could be advantages if there were photodiode properties that could change from one photodiode to another such as the spectral responsivity of the photodiode. A disadvantage is that the data must be collected at different points in time and therefore the tissue could be changing in time.

Although the preceding paragraphs describe specific embodiments where the components of the disclosed systems and devices can be included in one of the monitor 110, 309, or 609, the sensor 120, 301, 400, or 601, and the cable 130, the disclosure is not intended to be limited thereby. Rather, a skilled artisan will recognize from the disclosure herein that the components can individually be placed anywhere along the monitoring path in the monitor 110, 309, or 609, in the sensor 120, 301, 400, or 601, or in the cable 130, or in connectors associated with any of the foregoing, so long as the components may continue to perform their desired functionality. Further, one or more of the components may not be included in the system 400 in some implementations. For instance, the system 400 may not include one or both of the temperature sensor 438 and the heat pump 440.

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, methods, etc. described herein. A wide variety of variation is possible. Components, elements, and/or steps can be altered, added, removed, or rearranged. While certain embodiments have been explicitly described, other embodiments will become apparent to those of ordinary skill in the art based on this disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out altogether (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A physiological measurement system based on optical transmission spectroscopy comprising:
    an emitter configured to emit light at a wavelength;
    a first detector set at a shorter transmission path configured to detect a first beam of transmitted light, the detected light being attenuated by a sample tissue, the first detector further configured to output a first signal responsive to the detected light of the first beam; and
    a second detector fixed at a second, longer transmission path configured to detect a second beam of transmitted light and to output a second signal responsive to the detected light of the second beam; and a processor configured to receive signals responsive to the first and second signals to determine a bulk absorbance of an analyte in the sample tissue,
    wherein a thickness of the tissue is controlled at least in part by a depth stop such that a first distance between the emitter and the first detector is fixed to define a first known path length and a second distance between the emitter and the second detector is fixed to define a second known path length.

2. The optical physiological measurement system of claim 1, further comprising a first thermal controller, thermally coupled to the emitter, the first thermal controller configured to regulate a temperature of the emitter.

3. The optical physiological measurement system of claim 2, wherein the first thermal controller comprises a temperature sensor, a thermoelectric cooler, and a heat sink.

4. The optical physiological measurement system of claim 2, wherein the first thermal controller is further configured to modulate the temperature of the emitter to cause the emitter to emit light comprising a range of wavelengths.

5. The optical physiological measurement system of claim 4, wherein the thermal controller further comprises a thermoelectric cooler.

6. The optical physiological measurement system of claim 5, wherein the thermoelectric cooler comprises a Peltier device.

7. The optical physiological measurement system of claim 2, wherein the emitter further comprises an operational temperature and wherein the first thermal controller is further configured to cause a change to the emitter's operational temperature.

8. The optical physiological measurement system of claim 1, wherein the second detector is optically shielded.

9. The optical physiological measurement system of claim 1, comprising a second thermal controller, thermally coupled to the first detector, configured to control a temperature of the first detector.

10. The optical physiological measurement system of claim 9, comprising a third thermal controller, thermally coupled to the second detector, configured to control a temperature of the second detector.

11. The optical physiological measurement system of claim 10, further comprising a fourth thermal controller, thermally coupled to the sample tissue, the fourth thermal controller configured to measure a temperature of the sample tissue.

12. The optical physiological measurement system of claim 11, wherein the fourth thermal controller is further configured to regulate the temperature of the sample tissue.

13. The optical physiological measurement system of claim 1, wherein the analyte is at least one of glucose, water content, and hydration.

14. The optical physiological measurement system of claim 1, wherein the emitter is further configured to receive a drive signal, and wherein the processor is further configured to control the drive signal delivered to the emitter.

15. The optical physiological measurement system of claim 14, wherein the drive signal further comprises a drive current and a duty cycle, and wherein the processor is further configured to control and vary the drive current and/or the duty cycle.

16. The optical physiological measurement system of claim 1, further comprising an emitter that has an emission area between 1 mm-10 mm diameter.

17. The optical physiological measurement system of claim 1, wherein a difference in distance between the emitter and the first detector and the emitter and the second detector is 0.2 mm to 1 mm.

18. A method of varying light emitted in a physiological optical sensor, the method comprising:
  determining a temperature, a drive current, a forward voltage, and a duty cycle of a light emitter that emits light at a first wavelength at a first time;
  measuring, with a first detector, a first indication of a physiological parameter;
  altering at least one of the determined temperature, drive current, forward voltage, and duty cycle of the emitter at a second time to cause the emitter to emit light at a second wavelength; and
  measuring, with a second detector, a second indication of a physiological parameter,
  wherein a thickness of a tissue is controlled at least in part by a depth stop such that a first distance between the emitter and the first detector is fixed to define a first known path length and a second distance between the emitter and the second detector is fixed to define a second known path length.

19. The method of claim 18, wherein altering the determined temperature of the emitter comprises using a circuitry-based temperature alteration device or a thermal controller.

20. The method of claim 19, wherein the circuitry-based temperature alteration device or the thermal controller comprises a Peltier device.

* * * * *